US007368532B2

(12) United States Patent
Shone et al.

(10) Patent No.: US 7,368,532 B2
(45) Date of Patent: *May 6, 2008

(54) CONSTRUCTS FOR DELIVERY OF THERAPEUTIC AGENTS TO NEURONAL CELLS

(75) Inventors: Clifford Charles Shone, Salisbury (GB); John Mark Sutton, Salisbury (GB); Nigel Silman, Salisbury (GB)

(73) Assignee: Syntaxin Limited (GB)

( * ) Notice: Subject to any disclaimer, the term of this patent is extended or adjusted under 35 U.S.C. 154(b) by 893 days.

This patent is subject to a terminal disclaimer.

(21) Appl. No.: 10/130,973

(22) PCT Filed: Dec. 4, 2000

(86) PCT No.: PCT/GB00/04644

§ 371 (c)(1),
(2), (4) Date: Jun. 25, 2002

(87) PCT Pub. No.: WO01/58936

PCT Pub. Date: Aug. 16, 2001

(65) Prior Publication Data

US 2003/0147895 A1     Aug. 7, 2003

(30) Foreign Application Priority Data

Dec. 2, 1999  (GB) ................................. 9928530.6
Apr. 7, 2000  (GB) ................................. 0008658.7

(51) Int. Cl.
*C07K 1/00*    (2006.01)
*C07K 14/10*   (2006.01)
*C07K 17/00*   (2006.01)
*C07K 14/00*   (2006.01)
*C07K 16/00*   (2006.01)

(52) U.S. Cl. ....................................... 530/350; 530/402
(58) Field of Classification Search ................. 514/44; 536/23.1; 530/350, 402
See application file for complete search history.

(56) References Cited

U.S. PATENT DOCUMENTS

| 5,521,291 | A |   | 5/1996  | Curiel et al. |
| 5,668,255 | A | * | 9/1997  | Murphy ....................... 530/350 |
| 5,989,545 | A |   | 11/1999 | Foster et al. |
| 6,395,513 | B1 |  | 5/2002  | Foster et al. |
| 6,461,617 | B1 |  | 10/2002 | Shone et al. |
| 6,632,440 | B1 |  | 10/2003 | Quinn et al. |
| 2002/0044950 | A1 | | 4/2002 | Shone et al. |
| 2003/0049264 | A1 | | 3/2003 | Foster et al. |
| 2003/0166238 | A1 | | 9/2003 | Shone et al. |
| 2004/0071736 | A1 | | 4/2004 | Quinn et al. |

FOREIGN PATENT DOCUMENTS

EP  0 439 954 A2  8/1991
WO  WO 99/09057  2/1999
WO  WO 99/17806  4/1999
WO  WO 00/28041  5/2000
WO  WO 01/19863 A1  3/2001
WO  WO 01/36588 A2  5/2001

OTHER PUBLICATIONS

Francis, et al. (2004, Brain Research, 995:84-96).*
Halpern and Loftus (1993, JBC, 268:11188-11192).*
Kim et al., 2002, Stroke, 33: 809-815.*
Martin et al., 1998, Brain Research Bulletin, 46: 281-309.*
Humeau et al. 2000, Biocheimie, 82: 427-446.*
Mitsuya et al., 1985, PNAS, USA, 82: 7096-7100.*
Agrawal and Kanimalla 2000, Molecular Medicine Today, 61: 72-81.*
Figueiredo et al. 1997, Experimental Neurology, 145: 546-554.*
Lacy. et al., 1998, Nature Structural Biology, 5: 898-902.*
Application and Prosecution History for "Recombinant Toxin Fragments," Shone et al., U.S. Appl. No. 09/255,829, filed Feb. 23, 1999.
Application and Prosecution History for "Conjugates of Galatose-Binding Lectins and Clostridial Neurotoxins as Analgesics," Duggan et al., U.S. Appl. No. 09/529,130, with a §371 date Jun. 22, 2000.
Application and Prosecution History for "Methods and Compounds for the Treatment of Mucus Hypersecretion," Quinn et al., U.S. Appl. No. 09/763,669, with a §371 date May 29, 2001.
Application and Prosecution History for "Delivery of Superoxide Dismutase to Neuronal Cells," Shone et al., U.S. Appl. No. 09/831,050, with a §371 date of Aug. 20, 2001.
Application and Prosecution History for "Recombinant Toxin Fragments," Shone et al., U.S. Appl. No. 10/241,596, filed Sep. 12, 2002.
Application and Prosecution History for "Methods and Compounds for the Treatment of Mucus Hypersecretion," Quinn et al., U.S. Appl. No. 10/633,698, filed Aug. 5, 2003.
Shone et al., "Delivery of Superoxide Dismutase to Neuronal Cells," U.S. Appl. No. 11/062,471, filed Feb. 22, 2005.
Shone et al., "Recombinant Toxin Fragments," U.S. Appl. No. 11/077,550, filed Mar. 11, 2005.
Shone et al., "Recombinant Toxin Fragments," U.S. Appl. No. 10/527,411, filed Mar. 11, 2005.
International Search Report mailed Nov. 26, 2001 for International Application No. PCT/GB00/04644.
Helenius, A., et al., "Viruses as Tools in Drug Delivery," *Annels of the New York Academy of Sciences*, 507:1-6, New York Academy of Sciences (1987).

(Continued)

*Primary Examiner*—Anne Marie Wehbe'
*Assistant Examiner*—Joanne Hama
(74) *Attorney, Agent, or Firm*—Sterne, Kessler, Goldstein & Fox P.L.L.C

(57) ABSTRACT

A non-toxic polypeptide, for delivery of a therapeutic agent to a neuronal cell, comprises a binding domain that binds to the neuronal cell, and a translocation domain that translocates the therapeutic agent into the neuronal cell, wherein the translocation domain is not a $H_N$ domain of a clostridial toxin and is not a fragment or derivative of a $H_N$ domain of a clostridial toxin.

8 Claims, 7 Drawing Sheets

OTHER PUBLICATIONS

Figure 1:
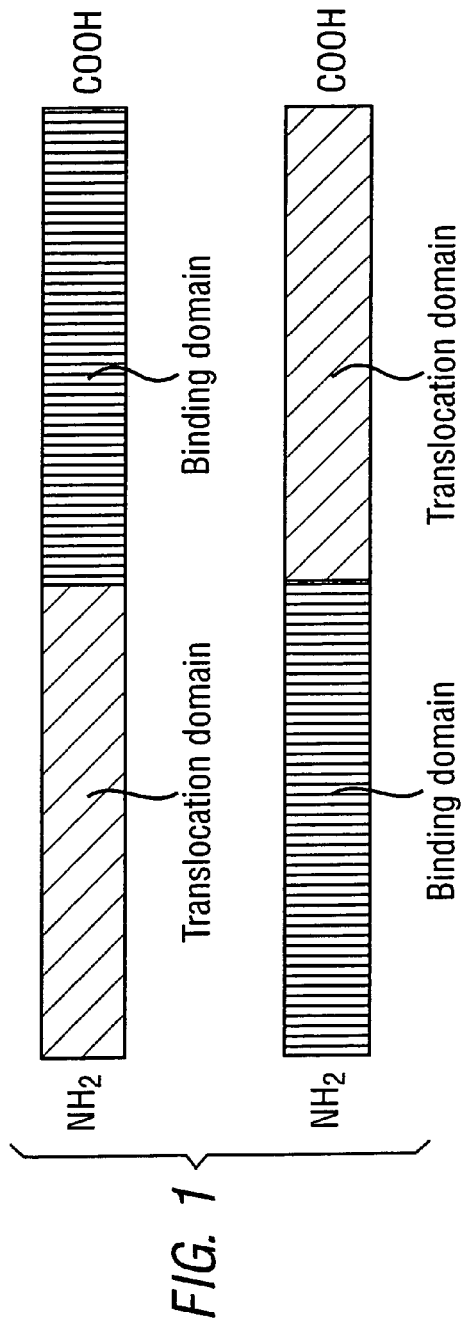

NLM Gateway abstract for Decout, A., et al., "Enhanced efficiency of a targeted fusogenic peptide," *Biochim. Biophys. Acta*. 1372:102-116, Elsevier Science B.V. (1998), accessed online Nov. 19, 2002 at <URL: http://gateway.nlm.nih.gov/gw/Cmd?GMResults>.

NLM Gateway abstract for Efremov, R.G., et al., "Factors important for fusogenic activity of peptides: molecular modeling study of analogs of fusion peptide of influenza virus hemagglutinin," *FEBS Lett. 462*: 205-210, Elsevier Science B.V. (1999), accessed online Nov. 19, 2002 at <URL: http://gateway.nlm.nih.gov/gw/Cmd?GMResults>.

NLM Gateway abstract for Kichler, A., et al., "Glycofection in the presence of anionic fusogenic peptides: a study of the parameters affecting the peptide-mediated enhancement of the transfection efficiency," *J. Gene Med. 1*: 134-143, John Wiley and Sons, Ltd. (1999), accessed online Nov. 19, 2002 at <URL: http://gateway.nlm.nih.gov/gw/Cmd?GMResults>.

NLM Gateway abstract for Martin, I., et al., "Membrane fusion induced by a short fusogenic peptide is assessed by its insertion and orientation into target bilayers," *Biochemistry*, 38: 9337-9347, American Chemical Society (1999), accessed online Nov. 19, 2002 at <URL: http://gateway.nlm.nih.gov/gw/Cmd?GMResults>.

NLM Gateway abstract for Tolstikov, V.V., et al., "Influence of endosome-destabilizing peptides on efficacy of anti-HIV immunotoxins," *Bioconjug. Chem.*, 8: 38-43, American Chemical Society (1997), accessed online Nov. 19, 2002 at <URL: http://gateway.nlm.nih.gov/gw/Cmd?GMResults>.

NLM Gateway abstract for Wagner, E., et al., "Influenza virus hemagglutinin HA-2 N-terminal fusogenic peptides augment gene transfer by tranferrin-polylysine-DNA complexes: toward a synthetic virus-like gene-transfer vehicle," *Proc. Natl. Acad. Sci. U.S. A.*, 89: 7934-7938, National Academy of Sciences (1992), accessed online Nov. 19, 2002 at <URL: http://gateway.nlm.nih.gov/gw/Cmd? GMResults>.

* cited by examiner

FIG. 3

Translocation — Binding  (SH)

Modified clostridial heavy chain fragment containing a translocation domain with a free sulphydryl group

+

Therapeutic polypeptide — SPDP

→

Binding — Translocation — (therapeutic polypeptide)

FIG. 6

[Graph: % Total Binding vs. Concentration Of Competing Unlabelled Ligand (Molar Excess)]

● Tetanus Neurotoxin
■ Modified Clostridial Heavy Chain

FIG. 7

% Control Value Binding (No Competing Ligand) vs Molar Excess Of Competing Construct ●— Competition Of $^{125}$I-Labeled BoNT/F Neuronal Binding By A Diphtheria-F/Hc Construct

FIG. 8

← Native Heavy Chain (type A)

← Modified Clostridial Heavy Chain (Diptheria $H_N$-BoNTH/F $H_C$)

*Key:*
Lane 1: High molecular weight Native markers; Pharmacia
Lane 2: Low molecular weight markers; Pharmacia
Lane 3: Native botulinum heavy chain (type A)
Lane 4: Modified Clostridial Heavy Chain (Diptheria $H_N$-BoNTH/F $H_C$)

SEQUENCE LISTING

<160> NUMBER OF SEQ ID NOS: 18

<210> SEQ ID NO 1
<211> LENGTH: 10
<212> TYPE: PRT
<213> ORGANISM: Artificial Sequence
<220> FEATURE:
<223> OTHER INFORMATION: synthetic construct

<400> SEQUENCE: 1

Cys Gly Leu Val Pro Ala Gly Ser Gly Pro

```
1               5                   10
```

<210> SEQ ID NO 2
<211> LENGTH: 17
<212> TYPE: PRT
<213> ORGANISM: Artificial Sequence
<220> FEATURE:
<223> OTHER INFORMATION: synthetic construct

<400> SEQUENCE: 2

Cys Gly Leu Val Pro Ala Gly Ser Gly Pro Ser Ala Gly Ser Ser Ala
1               5                   10                  15

Cys

<210> SEQ ID NO 3
<211> LENGTH: 882
<212> TYPE: PRT
<213> ORGANISM: Artificial Sequence
<220> FEATURE:
<223> OTHER INFORMATION: synthetic construct

<400> SEQUENCE: 3

Met Pro Phe Glu Leu Pro Ala Leu Pro Tyr Pro Tyr Asp Ala Leu Glu
1               5                   10                  15

Pro His Ile Asp Lys Glu Thr Met Asn Ile His His Thr Lys His His
            20                  25                  30

Asn Thr Tyr Val Thr Asn Leu Asn Ala Ala Leu Glu Gly His Pro Asp
        35                  40                  45

Leu Gln Asn Lys Ser Leu Glu Glu Leu Leu Ser Asn Leu Glu Ala Leu
    50                  55                  60

Pro Glu Ser Ile Arg Thr Ala Val Arg Asn Asn Gly Gly Gly His Ala
65                  70                  75                  80

Asn His Ser Leu Phe Trp Thr Ile Leu Ser Pro Asn Gly Gly Gly Glu
                85                  90                  95

Pro Thr Gly Glu Leu Ala Asp Ala Ile Asn Lys Lys Phe Gly Ser Phe
            100                 105                 110

Thr Ala Phe Lys Asp Glu Phe Ser Lys Ala Ala Ala Gly Arg Phe Gly
        115                 120                 125

Ser Gly Trp Ala Trp Leu Val Val Asn Asn Gly Glu Leu Glu Ile Thr
    130                 135                 140

Ser Thr Pro Asn Gln Asp Ser Pro Ile Met Glu Gly Lys Thr Pro Ile
145                 150                 155                 160

Leu Gly Leu Asp Val Trp Glu His Ala Tyr Tyr Leu Lys Tyr Gln Asn
                165                 170                 175

Arg Arg Pro Glu Tyr Ile Ala Ala Phe Trp Asn Val Val Asn Trp Asp
            180                 185                 190

Glu Val Ala Lys Arg Tyr Ser Glu Ala Lys Pro Lys Ser Gly Ser Cys
        195                 200                 205

Gly Leu Val Pro Arg Gly Ser Gly Pro Gly Ser Ser Val Gly Ser Ser
    210                 215                 220

Leu Ser Cys Ile Asn Leu Asp Trp Asp Val Ile Arg Asp Lys Thr Lys
225                 230                 235                 240

Thr Lys Ile Glu Ser Leu Lys Glu His Gly Pro Ile Lys Asn Lys Met
                245                 250                 255

Ser Glu Ser Pro Asn Lys Thr Val Ser Glu Glu Lys Ala Lys Gln Tyr
            260                 265                 270

Leu Glu Glu Phe His Gln Thr Ala Leu Glu His Pro Glu Leu Ser Glu

-continued

```
            275                 280                 285
Leu Lys Thr Val Thr Gly Thr Asn Pro Val Phe Ala Gly Ala Asn Tyr
290                 295                 300
Ala Ala Trp Ala Val Asn Val Ala Gln Val Ile Asp Ser Glu Thr Ala
305                 310                 315                 320
Asp Asn Leu Glu Lys Thr Thr Ala Ala Leu Ser Ile Leu Pro Gly Ile
                325                 330                 335
Gly Ser Val Met Gly Ile Ala Asp Gly Ala Val His His Asn Thr Glu
                340                 345                 350
Glu Ile Val Ala Gln Ser Ile Ala Leu Ser Ser Leu Met Val Ala Gln
                355                 360                 365
Ala Ile Pro Leu Val Gly Glu Leu Val Asp Ile Gly Phe Ala Ala Tyr
370                 375                 380
Asn Phe Val Glu Ser Ile Ile Asn Leu Phe Gln Val Val His Asn Ser
385                 390                 395                 400
Tyr Asn Arg Ser Ala Tyr Ser Pro Gly His Lys Thr Gln Pro Phe Leu
                405                 410                 415
His Asp Gly Tyr Ala Val Ser Trp Asn Thr Val Arg Ser Lys Asn Leu
                420                 425                 430
Asp Cys Trp Val Asp Asn Glu Glu Asp Ile Asp Val Ile Leu Lys Lys
                435                 440                 445
Ser Thr Ile Leu Asn Leu Asp Ile Asn Asn Asp Ile Ile Ser Asp Ile
                450                 455                 460
Ser Gly Phe Asn Ser Ser Val Ile Thr Tyr Pro Asp Ala Gln Leu Val
465                 470                 475                 480
Pro Gly Ile Asn Gly Lys Ala Ile His Leu Val Asn Asn Glu Ser Ser
                485                 490                 495
Glu Val Ile Val His Lys Ala Met Asp Ile Glu Tyr Asn Asp Met Phe
                500                 505                 510
Asn Asn Phe Thr Val Ser Phe Trp Leu Arg Val Pro Lys Val Ser Ala
                515                 520                 525
Ser His Leu Glu Gln Tyr Gly Thr Asn Glu Tyr Ser Ile Ile Ser Ser
530                 535                 540
Met Lys Lys His Ser Leu Ser Ile Gly Ser Gly Trp Ser Val Ser Leu
545                 550                 555                 560
Lys Gly Asn Asn Leu Ile Trp Thr Leu Lys Asp Ser Ala Gly Glu Val
                565                 570                 575
Arg Gln Ile Thr Phe Arg Asp Leu Pro Asp Lys Phe Asn Ala Tyr Leu
                580                 585                 590
Ala Asn Lys Trp Val Phe Ile Thr Ile Thr Asn Asp Arg Leu Ser Ser
                595                 600                 605
Ala Asn Leu Tyr Ile Asn Gly Val Leu Met Gly Ser Ala Glu Ile Thr
610                 615                 620
Gly Leu Gly Ala Ile Arg Glu Asp Asn Asn Ile Thr Leu Lys Leu Asp
625                 630                 635                 640
Arg Cys Asn Asn Asn Gln Tyr Val Ser Ile Asp Lys Phe Arg Ile
                645                 650                 655
Phe Cys Lys Ala Leu Asn Pro Lys Glu Ile Glu Lys Leu Tyr Thr Ser
                660                 665                 670
Tyr Leu Ser Ile Thr Phe Leu Arg Asp Phe Trp Gly Asn Pro Leu Arg
                675                 680                 685
Tyr Asp Thr Glu Tyr Tyr Leu Ile Pro Val Ala Ser Ser Lys Asp
690                 695                 700
```

```
Val Gln Leu Lys Asn Ile Thr Asp Tyr Met Tyr Leu Thr Asn Ala Pro
705                 710                 715                 720

Ser Tyr Thr Asn Gly Lys Leu Asn Ile Tyr Arg Arg Leu Tyr Asn
            725                 730                 735

Gly Leu Lys Phe Ile Ile Lys Arg Tyr Thr Pro Asn Asn Glu Ile Asp
            740                 745                 750

Ser Phe Val Lys Ser Gly Asp Phe Ile Lys Leu Tyr Val Ser Tyr Asn
            755                 760                 765

Asn Asn Glu His Ile Val Gly Tyr Pro Lys Asp Gly Asn Ala Phe Asn
770                 775                 780

Asn Leu Asp Arg Ile Leu Arg Val Gly Tyr Asn Ala Pro Gly Ile Pro
785                 790                 795                 800

Leu Tyr Lys Lys Met Glu Ala Val Lys Leu Arg Asp Leu Lys Thr Tyr
            805                 810                 815

Ser Val Gln Leu Lys Leu Tyr Asp Asp Lys Asn Ala Ser Leu Gly Leu
            820                 825                 830

Val Gly Thr His Asn Gly Gln Ile Gly Asn Asp Pro Asn Arg Asp Ile
            835                 840                 845

Leu Ile Ala Ser Asn Trp Tyr Phe Asn His Leu Lys Asp Lys Ile Leu
850                 855                 860

Gly Cys Asp Trp Tyr Phe Val Pro Thr Asp Gly Trp Thr Asn Asp
865                 870                 875                 880

Leu Gln

<210> SEQ ID NO 4
<211> LENGTH: 862
<212> TYPE: PRT
<213> ORGANISM: Artificial Sequence
<220> FEATURE:
<223> OTHER INFORMATION: synthetic construct

<400> SEQUENCE: 4

Met Pro Phe Glu Leu Pro Ala Leu Pro Tyr Pro Tyr Asp Ala Leu Glu
1               5                   10                  15

Pro His Ile Asp Lys Glu Thr Met Asn Ile His His Thr Lys His His
                20                  25                  30

Asn Thr Tyr Val Thr Asn Leu Asn Ala Ala Leu Glu Gly His Pro Asp
            35                  40                  45

Leu Gln Asn Lys Ser Leu Glu Glu Leu Leu Ser Asn Leu Glu Ala Leu
    50                  55                  60

Pro Glu Ser Ile Arg Thr Ala Val Arg Asn Asn Gly Gly His Ala
65                  70                  75                  80

Asn His Ser Leu Phe Trp Thr Ile Leu Ser Pro Asn Gly Gly Glu
                85                  90                  95

Pro Thr Gly Glu Leu Ala Asp Ala Ile Asn Lys Lys Phe Gly Ser Phe
            100                 105                 110

Thr Ala Phe Lys Asp Glu Phe Ser Lys Ala Ala Gly Arg Phe Gly
            115                 120                 125

Ser Gly Trp Ala Trp Leu Val Val Asn Asn Gly Glu Leu Glu Ile Thr
    130                 135                 140

Ser Thr Pro Asn Gln Asp Ser Pro Ile Met Glu Gly Lys Thr Pro Ile
145                 150                 155                 160

Leu Gly Leu Asp Val Trp Glu His Ala Tyr Tyr Leu Lys Tyr Gln Asn
                165                 170                 175
```

```
Arg Arg Pro Glu Tyr Ile Ala Ala Phe Trp Asn Val Val Asn Trp Asp
            180                 185                 190

Glu Val Ala Lys Arg Tyr Ser Glu Ala Lys Pro Lys Ser Gly Ser Cys
        195                 200                 205

Gly Ile Glu Gly Arg Ala Pro Gly Pro Gly Ser Ser Val Gly Ser Ser
        210                 215                 220

Leu Ser Cys Ile Asn Leu Asp Trp Asp Val Ile Arg Asp Lys Thr Lys
225                 230                 235                 240

Thr Lys Ile Glu Ser Leu Lys Glu His Gly Pro Ile Lys Asn Lys Met
                245                 250                 255

Ser Glu Ser Pro Asn Lys Thr Val Ser Glu Lys Ala Lys Gln Tyr
                260                 265                 270

Leu Glu Glu Phe His Gln Thr Ala Leu Glu His Pro Glu Leu Ser Glu
                275                 280                 285

Leu Lys Thr Val Thr Gly Thr Asn Pro Val Phe Ala Gly Ala Asn Tyr
        290                 295                 300

Ala Ala Trp Ala Val Asn Val Ala Gln Val Ile Asp Ser Glu Thr Ala
305                 310                 315                 320

Asp Asn Leu Glu Lys Thr Thr Ala Ala Leu Ser Ile Leu Pro Gly Ile
                325                 330                 335

Gly Ser Val Met Gly Ile Ala Asp Gly Ala Val His His Asn Thr Glu
                340                 345                 350

Glu Ile Val Ala Gln Ser Ile Ala Leu Ser Ser Leu Met Val Ala Gln
            355                 360                 365

Ala Ile Pro Leu Val Gly Glu Leu Val Asp Ile Gly Phe Ala Ala Tyr
            370                 375                 380

Asn Phe Val Glu Ser Ile Ile Asn Leu Phe Gln Val Val His Asn Ser
385                 390                 395                 400

Tyr Asn Arg Ser Ala Tyr Ser Pro Gly His Lys Thr Gln Pro Phe Leu
                405                 410                 415

His Asp Gly Tyr Ala Val Ser Trp Asn Thr Val Arg Ser Thr Met Ser
                420                 425                 430

Tyr Thr Asn Asp Lys Ile Leu Ile Leu Tyr Phe Asn Lys Leu Tyr Lys
            435                 440                 445

Lys Ile Lys Asp Asn Ser Ile Leu Asp Met Arg Tyr Glu Asn Asn Lys
        450                 455                 460

Phe Ile Asp Ile Ser Gly Tyr Gly Ser Asn Ile Ser Ile Asn Gly Asp
465                 470                 475                 480

Val Tyr Ile Tyr Ser Thr Asn Arg Asn Gln Phe Gly Ile Tyr Ser Ser
                485                 490                 495

Lys Pro Ser Glu Val Asn Ile Ala Gln Asn Asn Asp Ile Ile Tyr Asn
            500                 505                 510

Gly Arg Tyr Gln Asn Phe Ser Ile Ser Phe Trp Val Arg Ile Pro Lys
            515                 520                 525

Tyr Phe Asn Lys Val Asn Leu Asn Asn Glu Tyr Thr Ile Ile Asp Cys
        530                 535                 540

Ile Arg Asn Asn Asn Ser Gly Trp Lys Ile Ser Leu Asn Tyr Asn Lys
545                 550                 555                 560

Ile Ile Trp Thr Leu Gln Asp Thr Ala Gly Asn Asn Gln Lys Leu Val
                565                 570                 575

Phe Asn Tyr Thr Gln Met Ile Ser Ile Ser Asp Tyr Ile Asn Lys Trp
            580                 585                 590

Ile Phe Val Thr Ile Thr Asn Asn Arg Leu Gly Asn Ser Arg Ile Tyr
```

```
                595                 600                 605
Ile Asn Gly Asn Leu Ile Asp Glu Lys Ser Ile Ser Asn Leu Gly Asp
        610                 615                 620

Ile His Val Ser Asp Asn Ile Leu Phe Lys Ile Val Gly Cys Asn Asp
625                 630                 635                 640

Thr Arg Tyr Val Gly Ile Arg Tyr Phe Lys Val Phe Asp Thr Glu Leu
                645                 650                 655

Gly Lys Thr Glu Ile Glu Thr Leu Tyr Ser Asp Glu Pro Asp Pro Ser
        660                 665                 670

Ile Leu Lys Asp Phe Trp Gly Asn Tyr Leu Leu Tyr Asn Lys Arg Tyr
                675                 680                 685

Tyr Leu Leu Asn Leu Leu Arg Thr Asp Lys Ser Ile Thr Gln Asn Ser
    690                 695                 700

Asn Phe Leu Asn Ile Asn Gln Gln Arg Gly Val Tyr Gln Lys Pro Asn
705                 710                 715                 720

Ile Phe Ser Asn Thr Arg Leu Tyr Thr Gly Val Glu Val Ile Ile Arg
                725                 730                 735

Lys Asn Gly Ser Thr Asp Ile Ser Asn Thr Asp Asn Phe Val Arg Lys
        740                 745                 750

Asn Asp Leu Ala Tyr Ile Asn Val Val Asp Arg Asp Val Glu Tyr Arg
                755                 760                 765

Leu Tyr Ala Asp Ile Ser Ile Ala Lys Pro Glu Lys Ile Ile Lys Leu
    770                 775                 780

Ile Arg Thr Ser Asn Ser Asn Asn Ser Leu Gly Gln Ile Ile Val Met
785                 790                 795                 800

Asp Ser Ile Gly Asn Asn Cys Thr Met Asn Phe Gln Asn Asn Asn Gly
                805                 810                 815

Gly Asn Ile Gly Leu Leu Gly Phe His Ser Asn Asn Leu Val Ala Ser
        820                 825                 830

Ser Trp Tyr Tyr Asn Asn Ile Arg Lys Asn Thr Ser Ser Asn Gly Cys
                835                 840                 845

Phe Trp Ser Phe Ile Ser Lys Glu His Gly Trp Gln Glu Asn
    850                 855                 860

<210> SEQ ID NO 5
<211> LENGTH: 907
<212> TYPE: PRT
<213> ORGANISM: Artificial Sequence
<220> FEATURE:
<223> OTHER INFORMATION: synthetic construct

<400> SEQUENCE: 5

Met Leu Ser Arg Ala Val Cys Gly Thr Ser Arg Gln Leu Ala Pro Ala
1               5                   10                  15

Leu Gly Tyr Leu Gly Ser Arg Gln Lys His Ser Arg Gly Ser Pro Ala
            20                  25                  30

Leu Pro Tyr Pro Tyr Asp Ala Leu Glu Pro His Ile Asp Lys Glu Thr
        35                  40                  45

Met Asn Ile His His Thr Lys His His Asn Thr Tyr Val Thr Asn Leu
    50                  55                  60

Asn Ala Ala Leu Glu Gly His Pro Asp Leu Gln Asn Lys Ser Leu Glu
65                  70                  75                  80

Glu Leu Leu Ser Asn Leu Glu Ala Leu Pro Glu Ser Ile Arg Thr Ala
                85                  90                  95

Val Arg Asn Asn Gly Gly Gly His Ala Asn His Ser Leu Phe Trp Thr
```

```
                  100                 105                 110
Ile Leu Ser Pro Asn Gly Gly Glu Pro Thr Gly Glu Leu Ala Asp
            115                 120                 125

Ala Ile Asn Lys Lys Phe Gly Ser Phe Thr Ala Phe Lys Asp Glu Phe
130                 135                 140

Ser Lys Ala Ala Ala Gly Arg Phe Gly Ser Gly Trp Ala Trp Leu Val
145                 150                 155                 160

Val Asn Asn Gly Glu Leu Glu Ile Thr Ser Thr Pro Asn Gln Asp Ser
                165                 170                 175

Pro Ile Met Glu Gly Lys Thr Pro Ile Leu Gly Leu Asp Val Trp Glu
            180                 185                 190

His Ala Tyr Tyr Leu Lys Tyr Gln Asn Arg Arg Pro Glu Tyr Ile Ala
                195                 200                 205

Ala Phe Trp Asn Val Val Asn Trp Asp Glu Val Ala Lys Arg Tyr Ser
            210                 215                 220

Glu Ala Lys Pro Lys Ser Gly Ser Cys Gly Ile Glu Gly Arg Ala Pro
225                 230                 235                 240

Gly Pro Gly Ser Ser Val Gly Ser Ser Leu Ser Cys Ile Asn Leu Asp
                245                 250                 255

Trp Asp Val Ile Arg Asp Lys Thr Lys Thr Lys Ile Glu Ser Leu Lys
            260                 265                 270

Glu His Gly Pro Ile Lys Asn Lys Met Ser Glu Ser Pro Asn Lys Thr
        275                 280                 285

Val Ser Glu Glu Lys Ala Lys Gln Tyr Leu Glu Glu Phe His Gln Thr
        290                 295                 300

Ala Leu Glu His Pro Glu Leu Ser Glu Leu Lys Thr Val Thr Gly Thr
305                 310                 315                 320

Asn Pro Val Phe Ala Gly Ala Asn Tyr Ala Ala Trp Ala Val Asn Val
                325                 330                 335

Ala Gln Val Ile Asp Ser Glu Thr Ala Asp Asn Leu Glu Lys Thr Thr
            340                 345                 350

Ala Ala Leu Ser Ile Leu Pro Gly Ile Gly Ser Val Met Gly Ile Ala
        355                 360                 365

Asp Gly Ala Val His His Asn Thr Glu Glu Ile Val Ala Gln Ser Ile
    370                 375                 380

Ala Leu Ser Ser Leu Met Val Ala Gln Ala Ile Pro Leu Val Gly Glu
385                 390                 395                 400

Leu Val Asp Ile Gly Phe Ala Ala Tyr Asn Phe Val Glu Ser Ile Ile
                405                 410                 415

Asn Leu Phe Gln Val Val His Asn Ser Tyr Asn Arg Ser Ala Tyr Ser
            420                 425                 430

Pro Gly His Lys Thr Gln Pro Phe Leu His Asp Gly Tyr Ala Val Ser
        435                 440                 445

Trp Asn Thr Val Arg Ser Lys Asn Leu Asp Cys Trp Val Asp Asn Glu
    450                 455                 460

Glu Asp Ile Asp Val Ile Leu Lys Lys Ser Thr Ile Leu Asn Leu Asp
465                 470                 475                 480

Ile Asn Asn Asp Ile Ile Ser Asp Ile Ser Gly Phe Asn Ser Ser Val
                485                 490                 495

Ile Thr Tyr Pro Asp Ala Gln Leu Val Pro Gly Ile Asn Gly Lys Ala
            500                 505                 510

Ile His Leu Val Asn Asn Glu Ser Ser Glu Val Ile Val His Lys Ala
        515                 520                 525
```

Met Asp Ile Glu Tyr Asn Asp Met Phe Asn Asn Phe Thr Val Ser Phe
            530                 535                 540

Trp Leu Arg Val Pro Lys Val Ser Ala Ser His Leu Glu Gln Tyr Gly
545                 550                 555                 560

Thr Asn Glu Tyr Ser Ile Ile Ser Ser Met Lys Lys His Ser Leu Ser
                565                 570                 575

Ile Gly Ser Gly Trp Ser Val Ser Leu Lys Gly Asn Asn Leu Ile Trp
            580                 585                 590

Thr Leu Lys Asp Ser Ala Gly Glu Val Arg Gln Ile Thr Phe Arg Asp
        595                 600                 605

Leu Pro Asp Lys Phe Asn Ala Tyr Leu Ala Asn Lys Trp Val Phe Ile
    610                 615                 620

Thr Ile Thr Asn Asp Arg Leu Ser Ser Ala Asn Leu Tyr Ile Asn Gly
625                 630                 635                 640

Val Leu Met Gly Ser Ala Glu Ile Thr Gly Leu Gly Ala Ile Arg Glu
                645                 650                 655

Asp Asn Asn Ile Thr Leu Lys Leu Asp Arg Cys Asn Asn Asn Asn Gln
            660                 665                 670

Tyr Val Ser Ile Asp Lys Phe Arg Ile Phe Cys Lys Ala Leu Asn Pro
        675                 680                 685

Lys Glu Ile Glu Lys Leu Tyr Thr Ser Tyr Leu Ser Ile Thr Phe Leu
    690                 695                 700

Arg Asp Phe Trp Gly Asn Pro Leu Arg Tyr Asp Thr Glu Tyr Tyr Leu
705                 710                 715                 720

Ile Pro Val Ala Ser Ser Ser Lys Asp Val Gln Leu Lys Asn Ile Thr
                725                 730                 735

Asp Tyr Met Tyr Leu Thr Asn Ala Pro Ser Tyr Thr Asn Gly Lys Leu
            740                 745                 750

Asn Ile Tyr Tyr Arg Arg Leu Tyr Asn Gly Leu Lys Phe Ile Ile Lys
        755                 760                 765

Arg Tyr Thr Pro Asn Asn Glu Ile Asp Ser Phe Val Lys Ser Gly Asp
    770                 775                 780

Phe Ile Lys Leu Tyr Val Ser Tyr Asn Asn Asn Glu His Ile Val Gly
785                 790                 795                 800

Tyr Pro Lys Asp Gly Asn Ala Phe Asn Asn Leu Asp Arg Ile Leu Arg
                805                 810                 815

Val Gly Tyr Asn Ala Pro Gly Ile Pro Leu Tyr Lys Lys Met Glu Ala
            820                 825                 830

Val Lys Leu Arg Asp Leu Lys Thr Tyr Ser Val Gln Leu Lys Leu Tyr
        835                 840                 845

Asp Asp Lys Asn Ala Ser Leu Gly Leu Val Gly Thr His Asn Gly Gln
    850                 855                 860

Ile Gly Asn Asp Pro Asn Arg Asp Ile Leu Ile Ala Ser Asn Trp Tyr
865                 870                 875                 880

Phe Asn His Leu Lys Asp Lys Ile Leu Gly Cys Asp Trp Tyr Phe Val
                885                 890                 895

Pro Thr Asp Glu Gly Trp Thr Asn Asp Leu Gln
            900                 905

<210> SEQ ID NO 6
<211> LENGTH: 887
<212> TYPE: PRT
<213> ORGANISM: Artificial Sequence
<220> FEATURE:

<223> OTHER INFORMATION: synthetic construct

<400> SEQUENCE: 6

```
Met Leu Ser Arg Ala Val Cys Gly Thr Ser Arg Gln Leu Ala Pro Ala
1               5                   10                  15

Leu Gly Tyr Leu Gly Ser Arg Gln Lys His Ser Arg Gly Ser Pro Ala
            20                  25                  30

Leu Pro Tyr Pro Tyr Asp Ala Leu Glu Pro His Ile Asp Lys Glu Thr
        35                  40                  45

Met Asn Ile His His Thr Lys His His Asn Thr Tyr Val Thr Asn Leu
    50                  55                  60

Asn Ala Ala Leu Glu Gly His Pro Asp Leu Gln Asn Lys Ser Leu Glu
65                  70                  75                  80

Glu Leu Leu Ser Asn Leu Glu Ala Leu Pro Glu Ser Ile Arg Thr Ala
                85                  90                  95

Val Arg Asn Asn Gly Gly His Ala Asn His Ser Leu Phe Trp Thr
            100                 105                 110

Ile Leu Ser Pro Asn Gly Gly Gly Glu Pro Thr Gly Glu Leu Ala Asp
        115                 120                 125

Ala Ile Asn Lys Lys Phe Gly Ser Phe Thr Ala Phe Lys Asp Glu Phe
        130                 135                 140

Ser Lys Ala Ala Ala Gly Arg Phe Gly Ser Gly Trp Ala Trp Leu Val
145                 150                 155                 160

Val Asn Asn Gly Glu Leu Glu Ile Thr Ser Thr Pro Asn Gln Asp Ser
            165                 170                 175

Pro Ile Met Glu Gly Lys Thr Pro Ile Leu Gly Leu Asp Val Trp Glu
        180                 185                 190

His Ala Tyr Tyr Leu Lys Tyr Gln Asn Arg Arg Pro Glu Tyr Ile Ala
        195                 200                 205

Ala Phe Trp Asn Val Val Asn Trp Asp Glu Val Ala Lys Arg Tyr Ser
        210                 215                 220

Glu Ala Lys Pro Lys Ser Gly Ser Cys Gly Leu Val Pro Arg Gly Ser
225                 230                 235                 240

Gly Pro Gly Ser Ser Val Gly Ser Ser Leu Ser Cys Ile Asn Leu Asp
            245                 250                 255

Trp Asp Val Ile Arg Asp Lys Thr Lys Thr Lys Ile Glu Ser Leu Lys
        260                 265                 270

Glu His Gly Pro Ile Lys Asn Lys Met Ser Glu Ser Pro Asn Lys Thr
        275                 280                 285

Val Ser Glu Glu Lys Ala Lys Gln Tyr Leu Glu Glu Phe His Gln Thr
    290                 295                 300

Ala Leu Glu His Pro Glu Leu Ser Glu Leu Lys Thr Val Thr Gly Thr
305                 310                 315                 320

Asn Pro Val Phe Ala Gly Ala Asn Tyr Ala Ala Trp Ala Val Asn Val
            325                 330                 335

Ala Gln Val Ile Asp Ser Glu Thr Ala Asp Asn Leu Glu Lys Thr Thr
        340                 345                 350

Ala Ala Leu Ser Ile Leu Pro Gly Ile Gly Ser Val Met Gly Ile Ala
        355                 360                 365

Asp Gly Ala Val His His Asn Thr Glu Glu Ile Val Ala Gln Ser Ile
        370                 375                 380

Ala Leu Ser Ser Leu Met Val Ala Gln Ala Ile Pro Leu Val Gly Glu
385                 390                 395                 400
```

-continued

```
Leu Val Asp Ile Gly Phe Ala Ala Tyr Asn Phe Val Glu Ser Ile Ile
            405                 410                 415

Asn Leu Phe Gln Val Val His Asn Ser Tyr Asn Arg Ser Ala Tyr Ser
            420                 425                 430

Pro Gly His Lys Thr Gln Pro Phe Leu His Asp Gly Tyr Ala Val Ser
            435                 440                 445

Trp Asn Thr Val Arg Ser Thr Met Ser Tyr Thr Asn Asp Lys Ile Leu
            450                 455                 460

Ile Leu Tyr Phe Asn Lys Leu Tyr Lys Lys Ile Lys Asp Asn Ser Ile
465                 470                 475                 480

Leu Asp Met Arg Tyr Glu Asn Asn Lys Phe Ile Asp Ile Ser Gly Tyr
            485                 490                 495

Gly Ser Asn Ile Ser Ile Asn Gly Asp Val Tyr Ile Tyr Ser Thr Asn
            500                 505                 510

Arg Asn Gln Phe Gly Ile Tyr Ser Ser Lys Pro Ser Glu Val Asn Ile
            515                 520                 525

Ala Gln Asn Asn Asp Ile Ile Tyr Asn Gly Arg Tyr Gln Asn Phe Ser
            530                 535                 540

Ile Ser Phe Trp Val Arg Ile Pro Lys Tyr Phe Asn Lys Val Asn Leu
545                 550                 555                 560

Asn Asn Glu Tyr Thr Ile Ile Asp Cys Ile Arg Asn Asn Asn Ser Gly
            565                 570                 575

Trp Lys Ile Ser Leu Asn Tyr Asn Lys Ile Ile Trp Thr Leu Gln Asp
            580                 585                 590

Thr Ala Gly Asn Asn Gln Lys Leu Val Phe Asn Tyr Thr Gln Met Ile
            595                 600                 605

Ser Ile Ser Asp Tyr Ile Asn Lys Trp Ile Phe Val Thr Ile Thr Asn
            610                 615                 620

Asn Arg Leu Gly Asn Ser Arg Ile Tyr Ile Asn Gly Asn Leu Ile Asp
625                 630                 635                 640

Glu Lys Ser Ile Ser Asn Leu Gly Asp Ile His Val Ser Asp Asn Ile
            645                 650                 655

Leu Phe Lys Ile Val Gly Cys Asn Asp Thr Arg Tyr Val Gly Ile Arg
            660                 665                 670

Tyr Phe Lys Val Phe Asp Thr Glu Leu Gly Lys Thr Glu Ile Glu Thr
            675                 680                 685

Leu Tyr Ser Asp Glu Pro Asp Pro Ser Ile Leu Lys Asp Phe Trp Gly
            690                 695                 700

Asn Tyr Leu Leu Tyr Asn Lys Arg Tyr Tyr Leu Leu Asn Leu Leu Arg
705                 710                 715                 720

Thr Asp Lys Ser Ile Thr Gln Asn Ser Asn Phe Leu Asn Ile Asn Gln
            725                 730                 735

Gln Arg Gly Val Tyr Gln Lys Pro Asn Ile Phe Ser Asn Thr Arg Leu
            740                 745                 750

Tyr Thr Gly Val Glu Val Ile Ile Arg Lys Asn Gly Ser Thr Asp Ile
            755                 760                 765

Ser Asn Thr Asp Asn Phe Val Arg Lys Asn Asp Leu Ala Tyr Ile Asn
            770                 775                 780

Val Val Asp Arg Asp Val Glu Tyr Arg Leu Tyr Ala Asp Ile Ser Ile
785                 790                 795                 800

Ala Lys Pro Glu Lys Ile Ile Lys Leu Ile Arg Thr Ser Asn Ser Asn
            805                 810                 815

Asn Ser Leu Gly Gln Ile Ile Val Met Asp Ser Ile Gly Asn Asn Cys
```

-continued

```
                820                 825                 830
Thr Met Asn Phe Gln Asn Asn Gly Gly Asn Ile Gly Leu Leu Gly
        835                 840                 845

Phe His Ser Asn Asn Leu Val Ala Ser Ser Trp Tyr Tyr Asn Asn Ile
    850                 855                 860

Arg Lys Asn Thr Ser Ser Asn Gly Cys Phe Trp Ser Phe Ile Ser Lys
865                 870                 875                 880

Glu His Gly Trp Gln Glu Asn
                885

<210> SEQ ID NO 7
<211> LENGTH: 685
<212> TYPE: PRT
<213> ORGANISM: Artificial Sequence
<220> FEATURE:
<223> OTHER INFORMATION: synthetic construct

<400> SEQUENCE: 7

Met Pro Phe Glu Leu Pro Ala Leu Pro Tyr Pro Tyr Asp Ala Leu Glu
1               5                   10                  15

Pro His Ile Asp Lys Glu Thr Met Asn Ile His His Thr Lys His His
            20                  25                  30

Asn Thr Tyr Val Thr Asn Leu Asn Ala Ala Leu Glu Gly His Pro Asp
        35                  40                  45

Leu Gln Asn Lys Ser Leu Glu Glu Leu Leu Ser Asn Leu Glu Ala Leu
    50                  55                  60

Pro Glu Ser Ile Arg Thr Ala Val Arg Asn Asn Gly Gly Gly His Ala
65                  70                  75                  80

Asn His Ser Leu Phe Trp Thr Ile Leu Ser Pro Asn Gly Gly Gly Glu
                85                  90                  95

Pro Thr Gly Glu Leu Ala Asp Ala Ile Asn Lys Lys Phe Gly Ser Phe
            100                 105                 110

Thr Ala Phe Lys Asp Glu Phe Ser Lys Ala Ala Ala Gly Arg Phe Gly
        115                 120                 125

Ser Gly Trp Ala Trp Leu Val Val Asn Asn Gly Glu Leu Glu Ile Thr
    130                 135                 140

Ser Thr Pro Asn Gln Asp Ser Pro Ile Met Glu Gly Lys Thr Pro Ile
145                 150                 155                 160

Leu Gly Leu Asp Val Trp Glu His Ala Tyr Tyr Leu Lys Tyr Gln Asn
                165                 170                 175

Arg Arg Pro Glu Tyr Ile Ala Ala Phe Trp Asn Val Val Asn Trp Asp
            180                 185                 190

Glu Val Ala Lys Arg Tyr Ser Glu Ala Lys Pro Lys Ser Gly Ser Cys
        195                 200                 205

Gly Ile Glu Gly Arg Ala Pro Gly Pro Gly Ser Ser Val Gly Ser Ser
    210                 215                 220

Leu Ser Cys Ile Asn Gly Leu Phe Gly Ala Ile Ala Gly Phe Ile Glu
225                 230                 235                 240

Asn Gly Trp Glu Gly Met Ile Asp Gly Trp Tyr Gly Thr Met Ser Tyr
                245                 250                 255

Thr Asn Asp Lys Ile Leu Ile Leu Tyr Phe Asn Lys Leu Tyr Lys Lys
            260                 265                 270

Ile Lys Asp Asn Ser Ile Leu Asp Met Arg Tyr Glu Asn Asn Lys Phe
        275                 280                 285

Ile Asp Ile Ser Gly Tyr Gly Ser Asn Ile Ser Ile Asn Gly Asp Val
```

```
            290                 295                 300
Tyr Ile Tyr Ser Thr Asn Arg Asn Gln Phe Gly Ile Tyr Ser Ser Lys
305                 310                 315                 320

Pro Ser Glu Val Asn Ile Ala Gln Asn Asp Ile Ile Tyr Asn Gly
                325                 330                 335

Arg Tyr Gln Asn Phe Ser Ile Ser Phe Trp Val Arg Ile Pro Lys Tyr
                340                 345                 350

Phe Asn Lys Val Asn Leu Asn Asn Glu Tyr Thr Ile Ile Asp Cys Ile
                355                 360                 365

Arg Asn Asn Asn Ser Gly Trp Lys Ile Ser Leu Asn Tyr Asn Lys Ile
370                 375                 380

Ile Trp Thr Leu Gln Asp Thr Ala Gly Asn Asn Gln Lys Leu Val Phe
385                 390                 395                 400

Asn Tyr Thr Gln Met Ile Ser Ile Ser Asp Tyr Ile Asn Lys Trp Ile
                405                 410                 415

Phe Val Thr Ile Thr Asn Asn Arg Leu Gly Asn Ser Arg Ile Tyr Ile
                420                 425                 430

Asn Gly Asn Leu Ile Asp Glu Lys Ser Ile Ser Asn Leu Gly Asp Ile
                435                 440                 445

His Val Ser Asp Asn Ile Leu Phe Lys Ile Val Gly Cys Asn Asp Thr
                450                 455                 460

Arg Tyr Val Gly Ile Arg Tyr Phe Lys Val Phe Asp Thr Glu Leu Gly
465                 470                 475                 480

Lys Thr Glu Ile Glu Thr Leu Tyr Ser Asp Glu Pro Asp Pro Ser Ile
                485                 490                 495

Leu Lys Asp Phe Trp Gly Asn Tyr Leu Leu Tyr Asn Lys Arg Tyr Tyr
                500                 505                 510

Leu Leu Asn Leu Leu Arg Thr Asp Lys Ser Ile Thr Gln Asn Ser Asn
                515                 520                 525

Phe Leu Asn Ile Asn Gln Gln Arg Gly Val Tyr Gln Lys Pro Asn Ile
530                 535                 540

Phe Ser Asn Thr Arg Leu Tyr Thr Gly Val Glu Val Ile Ile Arg Lys
545                 550                 555                 560

Asn Gly Ser Thr Asp Ile Ser Asn Thr Asp Asn Phe Val Arg Lys Asn
                565                 570                 575

Asp Leu Ala Tyr Ile Asn Val Val Asp Arg Asp Val Glu Tyr Arg Leu
                580                 585                 590

Tyr Ala Asp Ile Ser Ile Ala Lys Pro Glu Lys Ile Ile Lys Leu Ile
                595                 600                 605

Arg Thr Ser Asn Ser Asn Asn Ser Leu Gly Gln Ile Ile Val Met Asp
610                 615                 620

Ser Ile Gly Asn Asn Cys Thr Met Asn Phe Gln Asn Asn Asn Gly Gly
625                 630                 635                 640

Asn Ile Gly Leu Leu Gly Phe His Ser Asn Asn Leu Val Ala Ser Ser
                645                 650                 655

Trp Tyr Tyr Asn Asn Ile Arg Lys Asn Thr Ser Ser Asn Gly Cys Phe
                660                 665                 670

Trp Ser Phe Ile Ser Lys Glu His Gly Trp Gln Glu Asn
                675                 680                 685
```

<210> SEQ ID NO 8
<211> LENGTH: 645
<212> TYPE: PRT
<213> ORGANISM: Artificial Sequence

```
<220> FEATURE:
<223> OTHER INFORMATION: synthetic construct

<400> SEQUENCE: 8

Gly Ser Ser Val Gly Ser Ser Leu Ser Cys Ile Asn Leu Asp Trp Asp
1               5                   10                  15

Val Ile Arg Asp Lys Thr Lys Thr Lys Ile Glu Ser Leu Lys Glu His
            20                  25                  30

Gly Pro Ile Lys Asn Lys Met Ser Glu Ser Pro Asn Lys Thr Val Ser
        35                  40                  45

Glu Glu Lys Ala Lys Gln Tyr Leu Glu Glu Phe His Gln Thr Ala Leu
50                  55                  60

Glu His Pro Glu Leu Ser Glu Leu Lys Thr Val Thr Gly Thr Asn Pro
65                  70                  75                  80

Val Phe Ala Gly Ala Asn Tyr Ala Ala Trp Ala Val Asn Val Ala Gln
                85                  90                  95

Val Ile Asp Ser Glu Thr Ala Asp Asn Leu Glu Lys Thr Thr Ala Ala
            100                 105                 110

Leu Ser Ile Leu Pro Gly Ile Gly Ser Val Met Gly Ile Ala Asp Gly
        115                 120                 125

Ala Val His His Asn Thr Glu Glu Ile Val Ala Gln Ser Ile Ala Leu
130                 135                 140

Ser Ser Leu Met Val Ala Gln Ala Ile Pro Leu Val Gly Glu Leu Val
145                 150                 155                 160

Asp Ile Gly Phe Ala Ala Tyr Asn Phe Val Glu Ser Ile Ile Asn Leu
                165                 170                 175

Phe Gln Val Val His Asn Ser Tyr Asn Arg Pro Ala Tyr Ser Pro Gly
            180                 185                 190

His Lys Thr Gln Pro Phe Leu His Asp Gly Tyr Ala Val Ser Trp Asn
        195                 200                 205

Thr Val Arg Ser Thr Met Ser Tyr Thr Asn Asp Lys Ile Leu Ile Leu
210                 215                 220

Tyr Phe Asn Lys Leu Tyr Lys Lys Ile Lys Asp Asn Ser Ile Leu Asp
225                 230                 235                 240

Met Arg Tyr Glu Asn Asn Lys Phe Ile Asp Ile Ser Gly Tyr Gly Ser
                245                 250                 255

Asn Ile Ser Ile Asn Gly Asp Val Tyr Ile Tyr Ser Thr Asn Arg Asn
            260                 265                 270

Gln Phe Gly Ile Tyr Ser Ser Lys Pro Ser Glu Val Asn Ile Ala Gln
        275                 280                 285

Asn Asn Asp Ile Ile Tyr Asn Gly Arg Tyr Gln Asn Phe Ser Ile Ser
290                 295                 300

Phe Trp Val Arg Ile Pro Lys Tyr Phe Asn Lys Val Asn Leu Asn Asn
305                 310                 315                 320

Glu Tyr Thr Ile Ile Asp Cys Ile Arg Asn Asn Asn Ser Gly Trp Lys
                325                 330                 335

Ile Ser Leu Asn Tyr Asn Lys Ile Ile Trp Thr Leu Gln Asp Thr Ala
            340                 345                 350

Gly Asn Asn Gln Lys Leu Val Phe Asn Tyr Thr Gln Met Ile Ser Ile
        355                 360                 365

Ser Asp Tyr Ile Asn Lys Trp Ile Phe Val Thr Ile Thr Asn Asn Arg
370                 375                 380

Leu Gly Asn Ser Arg Ile Tyr Ile Asn Gly Asn Leu Ile Asp Glu Lys
385                 390                 395                 400
```

-continued

```
Ser Ile Ser Asn Leu Gly Asp Ile His Val Ser Asp Asn Ile Leu Phe
                405                 410                 415

Lys Ile Val Gly Cys Asn Asp Thr Arg Tyr Val Gly Ile Arg Tyr Phe
            420                 425                 430

Lys Val Phe Asp Thr Glu Leu Gly Lys Thr Glu Ile Glu Thr Leu Tyr
        435                 440                 445

Ser Asp Glu Pro Asp Pro Ser Ile Leu Lys Asp Phe Trp Gly Asn Tyr
    450                 455                 460

Leu Leu Tyr Asn Lys Arg Tyr Tyr Leu Leu Asn Leu Leu Arg Thr Asp
465                 470                 475                 480

Lys Ser Ile Thr Gln Asn Ser Asn Phe Leu Asn Ile Asn Gln Gln Arg
                485                 490                 495

Gly Val Tyr Gln Lys Pro Asn Ile Phe Ser Asn Thr Arg Leu Tyr Thr
            500                 505                 510

Gly Val Glu Val Ile Ile Arg Lys Asn Gly Ser Thr Asp Ile Ser Asn
        515                 520                 525

Thr Asp Asn Phe Val Arg Lys Asn Asp Leu Ala Tyr Ile Asn Val Val
    530                 535                 540

Asp Arg Asp Val Glu Tyr Arg Leu Tyr Ala Asp Ile Ser Ile Ala Lys
545                 550                 555                 560

Pro Glu Lys Ile Ile Lys Leu Ile Arg Thr Ser Asn Ser Asn Asn Ser
                565                 570                 575

Leu Gly Gln Ile Ile Val Met Asp Ser Ile Gly Asn Asn Cys Thr Met
            580                 585                 590

Asn Phe Gln Asn Asn Asn Gly Gly Asn Ile Gly Leu Leu Gly Phe His
        595                 600                 605

Ser Asn Asn Leu Val Ala Ser Ser Trp Tyr Tyr Asn Asn Ile Arg Lys
    610                 615                 620

Asn Thr Ser Ser Asn Gly Cys Phe Trp Ser Phe Ile Ser Lys Glu His
625                 630                 635                 640

Gly Trp Gln Glu Asn
                645

<210> SEQ ID NO 9
<211> LENGTH: 665
<212> TYPE: PRT
<213> ORGANISM: Artificial Sequence
<220> FEATURE:
<223> OTHER INFORMATION: synthetic construct

<400> SEQUENCE: 9

Gly Ser Ser Val Gly Ser Ser Leu Ser Cys Ile Asn Leu Asp Trp Asp
1               5                   10                  15

Val Ile Arg Asp Lys Thr Lys Thr Lys Ile Glu Ser Leu Lys Glu His
            20                  25                  30

Gly Pro Ile Lys Asn Lys Met Ser Glu Ser Pro Asn Lys Thr Val Ser
        35                  40                  45

Glu Glu Lys Ala Lys Gln Tyr Leu Glu Glu Phe His Gln Thr Ala Leu
    50                  55                  60

Glu His Pro Glu Leu Ser Glu Leu Lys Thr Val Thr Gly Thr Asn Pro
65                  70                  75                  80

Val Phe Ala Gly Ala Asn Tyr Ala Ala Trp Ala Val Asn Val Ala Gln
                85                  90                  95

Val Ile Asp Ser Glu Thr Ala Asp Asn Leu Glu Lys Thr Thr Ala Ala
            100                 105                 110
```

-continued

Leu Ser Ile Leu Pro Gly Ile Gly Ser Val Met Gly Ile Ala Asp Gly
                115                 120                 125

Ala Val His His Asn Thr Glu Glu Ile Val Ala Gln Ser Ile Ala Leu
            130                 135                 140

Ser Ser Leu Met Val Ala Gln Ala Ile Pro Leu Val Gly Glu Leu Val
145                 150                 155                 160

Asp Ile Gly Phe Ala Ala Tyr Asn Phe Val Glu Ser Ile Ile Asn Leu
                165                 170                 175

Phe Gln Val Val His Asn Ser Tyr Asn Arg Pro Ala Tyr Ser Pro Gly
            180                 185                 190

His Lys Thr Gln Pro Phe Leu His Asp Gly Tyr Ala Val Ser Trp Asn
            195                 200                 205

Thr Val Arg Ser Lys Asn Leu Asp Cys Trp Val Asp Asn Glu Glu Asp
            210                 215                 220

Ile Asp Val Ile Leu Lys Lys Ser Thr Ile Leu Asn Leu Asp Ile Asn
225                 230                 235                 240

Asn Asp Ile Ile Ser Asp Ile Ser Gly Phe Asn Ser Ser Val Ile Thr
                245                 250                 255

Tyr Pro Asp Ala Gln Leu Val Pro Gly Ile Asn Gly Lys Ala Ile His
            260                 265                 270

Leu Val Asn Asn Glu Ser Ser Glu Val Ile Val His Lys Ala Met Asp
            275                 280                 285

Ile Glu Tyr Asn Asp Met Phe Asn Asn Phe Thr Val Ser Phe Trp Leu
            290                 295                 300

Arg Val Pro Lys Val Ser Ala Ser His Leu Glu Gln Tyr Gly Thr Asn
305                 310                 315                 320

Glu Tyr Ser Ile Ile Ser Ser Met Lys Lys His Ser Leu Ser Ile Gly
                325                 330                 335

Ser Gly Trp Ser Val Ser Leu Lys Gly Asn Asn Leu Ile Trp Thr Leu
            340                 345                 350

Lys Asp Ser Ala Gly Glu Val Arg Gln Ile Thr Phe Arg Asp Leu Pro
            355                 360                 365

Asp Lys Phe Asn Ala Tyr Leu Ala Asn Lys Trp Val Phe Ile Thr Ile
            370                 375                 380

Thr Asn Asp Arg Leu Ser Ser Ala Asn Leu Tyr Ile Asn Gly Val Leu
385                 390                 395                 400

Met Gly Ser Ala Glu Ile Thr Gly Leu Gly Ala Ile Arg Glu Asp Asn
                405                 410                 415

Asn Ile Thr Leu Lys Leu Asp Arg Cys Asn Asn Asn Asn Gln Tyr Val
            420                 425                 430

Ser Ile Asp Lys Phe Arg Ile Phe Cys Lys Ala Leu Asn Pro Lys Glu
            435                 440                 445

Ile Glu Lys Leu Tyr Thr Ser Tyr Leu Ser Ile Thr Phe Leu Arg Asp
            450                 455                 460

Phe Trp Gly Asn Pro Leu Arg Tyr Asp Thr Glu Tyr Tyr Leu Ile Pro
465                 470                 475                 480

Val Ala Ser Ser Ser Lys Asp Val Gln Leu Lys Asn Ile Thr Asp Tyr
                485                 490                 495

Met Tyr Leu Thr Asn Ala Pro Ser Tyr Thr Asn Gly Lys Leu Asn Ile
            500                 505                 510

Tyr Tyr Arg Arg Leu Tyr Asn Gly Leu Lys Phe Ile Ile Lys Arg Tyr
            515                 520                 525

```
Thr Pro Asn Asn Glu Ile Asp Ser Phe Val Lys Ser Gly Asp Phe Ile
    530                 535                 540

Lys Leu Tyr Val Ser Tyr Asn Asn Glu His Ile Val Gly Tyr Pro
545                 550                 555                 560

Lys Asp Gly Asn Ala Phe Asn Asn Leu Asp Arg Ile Leu Arg Val Gly
                565                 570                 575

Tyr Asn Ala Pro Gly Ile Pro Leu Tyr Lys Lys Met Glu Ala Val Lys
                580                 585                 590

Leu Arg Asp Leu Lys Thr Tyr Ser Val Gln Leu Lys Leu Tyr Asp Asp
                595                 600                 605

Lys Asn Ala Ser Leu Gly Leu Val Gly Thr His Asn Gly Gln Ile Gly
    610                 615                 620

Asn Asp Pro Asn Arg Asp Ile Leu Ile Ala Ser Asn Trp Tyr Phe Asn
625                 630                 635                 640

His Leu Lys Asp Lys Ile Leu Gly Cys Asp Trp Tyr Phe Val Pro Thr
                645                 650                 655

Asp Glu Gly Trp Thr Asn Asp Leu Gln
                660                 665

<210> SEQ ID NO 10
<211> LENGTH: 448
<212> TYPE: PRT
<213> ORGANISM: Artificial Sequence
<220> FEATURE:
<223> OTHER INFORMATION: synthetic construct

<400> SEQUENCE: 10

Gly Ser Ser Val Gly Ser Ser Leu Ser Cys Ile Asn Leu Asp Trp Asp
1               5                   10                  15

Val Ile Arg Asp Lys Thr Lys Thr Lys Ile Glu Ser Leu Lys Glu His
                20                  25                  30

Gly Pro Ile Lys Asn Lys Met Ser Glu Ser Pro Asn Lys Thr Val Ser
            35                  40                  45

Glu Glu Lys Ala Lys Gln Tyr Leu Glu Phe His Gln Thr Ala Leu
    50                  55                  60

Glu His Pro Glu Leu Ser Glu Leu Lys Thr Val Thr Gly Thr Asn Pro
65                  70                  75                  80

Val Phe Ala Gly Ala Asn Tyr Ala Ala Trp Ala Val Asn Val Ala Gln
                85                  90                  95

Val Ile Asp Ser Glu Thr Ala Asp Asn Leu Glu Lys Thr Thr Ala Ala
                100                 105                 110

Leu Ser Ile Leu Pro Gly Ile Gly Ser Val Met Gly Ile Ala Asp Gly
            115                 120                 125

Ala Val His His Asn Thr Glu Glu Ile Val Ala Gln Ser Ile Ala Leu
    130                 135                 140

Ser Ser Leu Met Val Ala Gln Ala Ile Pro Leu Val Gly Glu Leu Val
145                 150                 155                 160

Asp Ile Gly Phe Ala Ala Tyr Asn Phe Val Glu Ser Ile Ile Asn Leu
                165                 170                 175

Phe Gln Val Val His Asn Ser Tyr Asn Arg Pro Ala Tyr Ser Pro Gly
                180                 185                 190

His Lys Thr Gln Pro Phe Leu His Asp Gly Tyr Ala Val Ser Trp Asn
            195                 200                 205

Thr Val Arg Ser Val Tyr Val Ser Ile Asp Lys Phe Arg Ile Phe Cys
    210                 215                 220
```

```
Lys Ala Leu Asn Pro Lys Glu Ile Glu Lys Leu Tyr Thr Ser Tyr Leu
225                 230                 235                 240

Ser Ile Thr Phe Leu Arg Asp Phe Trp Gly Asn Pro Leu Arg Tyr Asp
            245                 250                 255

Thr Glu Tyr Tyr Leu Ile Pro Val Ala Ser Ser Lys Asp Val Gln
        260                 265                 270

Leu Lys Asn Ile Thr Asp Tyr Met Tyr Leu Thr Asn Ala Pro Ser Tyr
            275                 280                 285

Thr Asn Gly Lys Leu Asn Ile Tyr Tyr Arg Arg Leu Tyr Asn Gly Leu
    290                 295                 300

Lys Phe Ile Ile Lys Arg Tyr Thr Pro Asn Asn Glu Ile Asp Ser Phe
305                 310                 315                 320

Val Lys Ser Gly Asp Phe Ile Lys Leu Tyr Val Ser Tyr Asn Asn
                325                 330                 335

Glu His Ile Val Gly Tyr Pro Lys Asp Gly Asn Ala Phe Asn Asn Leu
            340                 345                 350

Asp Arg Ile Leu Arg Val Gly Tyr Asn Ala Pro Gly Ile Pro Leu Tyr
        355                 360                 365

Lys Lys Met Glu Ala Val Lys Leu Arg Asp Leu Lys Thr Tyr Ser Val
        370                 375                 380

Gln Leu Lys Leu Tyr Asp Asp Lys Asn Ala Ser Leu Gly Leu Val Gly
385                 390                 395                 400

Thr His Asn Gly Gln Ile Gly Asn Asp Pro Asn Arg Asp Ile Leu Ile
                405                 410                 415

Ala Ser Asn Trp Tyr Phe Asn His Leu Lys Asp Lys Ile Leu Gly Cys
            420                 425                 430

Asp Trp Tyr Phe Val Pro Thr Asp Glu Gly Trp Thr Asn Asp Leu Gln
        435                 440                 445

<210> SEQ ID NO 11
<211> LENGTH: 605
<212> TYPE: PRT
<213> ORGANISM: Artificial Sequence
<220> FEATURE:
<223> OTHER INFORMATION: synthetic construct

<400> SEQUENCE: 11

Gly Ser Ser Val Gly Ser Ser Leu Ser Cys Ile Asn Leu Asp Trp Asp
1               5                   10                  15

Val Ile Arg Asp Lys Thr Lys Thr Lys Ile Glu Ser Leu Lys Glu His
                20                  25                  30

Gly Pro Ile Lys Asn Lys Met Ser Glu Ser Pro Asn Lys Thr Val Ser
            35                  40                  45

Glu Glu Lys Ala Lys Gln Tyr Leu Glu Glu Phe His Gln Thr Ala Leu
    50                  55                  60

Glu His Pro Glu Leu Ser Glu Leu Lys Thr Val Thr Gly Thr Asn Pro
65                  70                  75                  80

Val Phe Ala Gly Ala Asn Tyr Ala Ala Trp Ala Val Asn Val Ala Gln
                85                  90                  95

Val Ile Asp Ser Glu Thr Ala Asp Asn Leu Glu Lys Thr Thr Ala Ala
            100                 105                 110

Leu Ser Ile Leu Pro Gly Ile Gly Ser Val Met Gly Ile Ala Asp Gly
        115                 120                 125

Ala Val His His Asn Thr Glu Glu Ile Val Ala Gln Ser Ile Ala Leu
    130                 135                 140
```

-continued

```
Ser Ser Leu Met Val Ala Gln Ala Ile Pro Leu Val Gly Glu Leu Val
145                 150                 155                 160

Asp Ile Gly Phe Ala Ala Tyr Asn Phe Val Glu Ser Ile Ile Asn Leu
                165                 170                 175

Phe Gln Val Val His Asn Ser Tyr Asn Arg Pro Ala Tyr Ser Pro Gly
            180                 185                 190

His Lys Thr Gln Pro Phe Leu His Asp Gly Tyr Ala Val Ser Trp Asn
        195                 200                 205

Thr Val Arg Ser Val Tyr Asn Asn Glu Ser Ser Glu Val Ile Val His
    210                 215                 220

Lys Ala Met Asp Ile Glu Tyr Asn Asp Met Phe Asn Asn Phe Thr Val
225                 230                 235                 240

Ser Phe Trp Leu Arg Val Pro Lys Val Ser Ala Ser His Leu Glu Gln
                245                 250                 255

Tyr Gly Thr Asn Glu Tyr Ser Ile Ile Ser Ser Met Lys Lys His Ser
            260                 265                 270

Leu Ser Ile Gly Ser Gly Trp Ser Val Ser Leu Lys Gly Asn Asn Leu
        275                 280                 285

Ile Trp Thr Leu Lys Asp Ser Ala Gly Glu Val Arg Gln Ile Thr Phe
    290                 295                 300

Arg Asp Leu Pro Asp Lys Phe Asn Ala Tyr Leu Ala Asn Lys Trp Val
305                 310                 315                 320

Phe Ile Thr Ile Thr Asn Asp Arg Leu Ser Ser Ala Asn Leu Tyr Ile
                325                 330                 335

Asn Gly Val Leu Met Gly Ser Ala Glu Ile Thr Gly Leu Gly Ala Ile
            340                 345                 350

Arg Glu Asp Asn Asn Ile Thr Leu Lys Leu Asp Arg Cys Asn Asn Asn
        355                 360                 365

Asn Gln Tyr Val Ser Ile Asp Lys Phe Arg Ile Phe Cys Lys Ala Leu
    370                 375                 380

Asn Pro Lys Glu Ile Glu Lys Leu Tyr Thr Ser Tyr Leu Ser Ile Thr
385                 390                 395                 400

Phe Leu Arg Asp Phe Trp Gly Asn Pro Leu Arg Tyr Asp Thr Glu Tyr
                405                 410                 415

Tyr Leu Ile Pro Val Ala Ser Ser Ser Lys Asp Val Gln Leu Lys Asn
            420                 425                 430

Ile Thr Asp Tyr Met Tyr Leu Thr Asn Ala Pro Ser Tyr Thr Asn Gly
        435                 440                 445

Lys Leu Asn Ile Tyr Tyr Arg Arg Leu Tyr Asn Gly Leu Lys Phe Ile
    450                 455                 460

Ile Lys Arg Tyr Thr Pro Asn Asn Glu Ile Asp Ser Phe Val Lys Ser
465                 470                 475                 480

Gly Asp Phe Ile Lys Leu Tyr Val Ser Tyr Asn Asn Asn Glu His Ile
                485                 490                 495

Val Gly Tyr Pro Lys Asp Gly Asn Ala Phe Asn Asn Leu Asp Arg Ile
            500                 505                 510

Leu Arg Val Gly Tyr Asn Ala Pro Gly Ile Pro Leu Tyr Lys Lys Met
        515                 520                 525

Glu Ala Val Lys Leu Arg Asp Leu Lys Thr Tyr Ser Val Gln Leu Lys
    530                 535                 540

Leu Tyr Asp Asp Lys Asn Ala Ser Leu Gly Leu Val Gly Thr His Asn
545                 550                 555                 560

Gly Gln Ile Gly Asn Asp Pro Asn Arg Asp Ile Leu Ile Ala Ser Asn
```

```
                565                 570                 575
Trp Tyr Phe Asn His Leu Lys Asp Lys Ile Leu Gly Cys Asp Trp Tyr
            580                 585                 590
Phe Val Pro Thr Asp Glu Gly Trp Thr Asn Asp Leu Gln
            595                 600             605

<210> SEQ ID NO 12
<211> LENGTH: 660
<212> TYPE: PRT
<213> ORGANISM: Artificial Sequence
<220> FEATURE:
<223> OTHER INFORMATION: synthetic construct

<400> SEQUENCE: 12

Gly Ser Ser Val Gly Ser Ser Leu Ser Cys Ile Asn Leu Asp Trp Asp
1               5                   10                  15
Val Ile Arg Asp Lys Thr Lys Thr Lys Ile Glu Ser Leu Lys Glu His
            20                  25                  30
Gly Pro Ile Lys Asn Lys Met Ser Glu Ser Pro Asn Lys Thr Val Ser
        35                  40                  45
Glu Glu Lys Ala Lys Gln Tyr Leu Glu Glu Phe His Gln Thr Ala Leu
    50                  55                  60
Glu His Pro Glu Leu Ser Glu Leu Lys Thr Val Thr Gly Thr Asn Pro
65                  70                  75                  80
Val Phe Ala Gly Ala Asn Tyr Ala Ala Trp Ala Val Asn Val Ala Gln
                85                  90                  95
Val Ile Asp Ser Glu Thr Ala Asp Asn Leu Glu Lys Thr Thr Ala Ala
            100                 105                 110
Leu Ser Ile Leu Pro Gly Ile Gly Ser Val Met Gly Ile Ala Asp Gly
        115                 120                 125
Ala Val His His Asn Thr Glu Glu Ile Val Ala Gln Ser Ile Ala Leu
    130                 135                 140
Ser Ser Leu Met Val Ala Gln Ala Ile Pro Leu Val Gly Glu Leu Val
145                 150                 155                 160
Asp Ile Gly Phe Ala Ala Tyr Asn Phe Val Glu Ser Ile Ile Asn Leu
                165                 170                 175
Phe Gln Val Val His Asn Ser Tyr Asn Arg Pro Ala Tyr Ser Pro Gly
            180                 185                 190
His Lys Thr Gln Pro Phe Leu His Asp Gly Tyr Ala Val Ser Trp Asn
        195                 200                 205
Thr Val Arg Ser Thr Met Ser Tyr Thr Asn Asp Lys Ile Leu Ile Leu
    210                 215                 220
Tyr Phe Asn Lys Leu Tyr Lys Lys Ile Lys Asp Asn Ser Ile Leu Asp
225                 230                 235                 240
Met Arg Tyr Glu Asn Asn Lys Phe Ile Asp Ile Ser Gly Tyr Gly Ser
                245                 250                 255
Asn Ile Ser Ile Asn Gly Asp Val Tyr Ile Tyr Ser Thr Asn Arg Asn
            260                 265                 270
Gln Phe Gly Ile Tyr Ser Ser Lys Pro Ser Glu Val Asn Ile Ala Gln
        275                 280                 285
Asn Asn Asp Ile Ile Tyr Asn Gly Arg Tyr Gln Asn Phe Ser Ile Ser
    290                 295                 300
Phe Trp Val Arg Ile Pro Lys Tyr Phe Asn Lys Val Asn Leu Asn Asn
305                 310                 315                 320
Glu Tyr Thr Ile Ile Asp Cys Ile Arg Asn Asn Asn Ser Gly Trp Lys
```

-continued

```
                325                 330                 335
Ile Ser Leu Asn Tyr Asn Lys Ile Ile Trp Thr Leu Gln Asp Thr Ala
            340                 345                 350
Gly Asn Asn Gln Lys Leu Val Phe Asn Tyr Thr Gln Met Ile Ser Ile
        355                 360                 365

Ser Asp Tyr Ile Asn Lys Trp Ile Phe Val Thr Ile Thr Asn Asn Arg
    370                 375                 380

Leu Gly Asn Ser Arg Ile Tyr Ile Asn Gly Asn Leu Ile Asp Glu Lys
385                 390                 395                 400
Ser Ile Ser Asn Leu Gly Asp Ile His Val Ser Asp Asn Ile Leu Phe
                405                 410                 415
Lys Ile Val Gly Cys Asn Asp Thr Arg Tyr Val Ser Ile Asp Lys Phe
            420                 425                 430

Arg Ile Phe Cys Lys Ala Leu Asn Pro Lys Glu Ile Glu Lys Leu Tyr
        435                 440                 445

Thr Ser Tyr Leu Ser Ile Thr Phe Leu Arg Asp Phe Trp Gly Asn Pro
    450                 455                 460

Leu Arg Tyr Asp Thr Glu Tyr Tyr Leu Ile Pro Val Ala Ser Ser Ser
465                 470                 475                 480
Lys Asp Val Gln Leu Lys Asn Ile Thr Asp Tyr Met Tyr Leu Thr Asn
                485                 490                 495
Ala Pro Ser Tyr Thr Asn Gly Lys Leu Asn Ile Tyr Tyr Arg Arg Leu
            500                 505                 510
Tyr Asn Gly Leu Lys Phe Ile Ile Lys Arg Tyr Thr Pro Asn Asn Glu
        515                 520                 525

Ile Asp Ser Phe Val Lys Ser Gly Asp Phe Ile Lys Leu Tyr Val Ser
    530                 535                 540

Tyr Asn Asn Asn Glu His Ile Val Gly Tyr Pro Lys Asp Gly Asn Ala
545                 550                 555                 560
Phe Asn Asn Leu Asp Arg Ile Leu Arg Val Gly Tyr Asn Ala Pro Gly
                565                 570                 575
Ile Pro Leu Tyr Lys Lys Met Glu Ala Val Lys Leu Arg Asp Leu Lys
            580                 585                 590
Thr Tyr Ser Val Gln Leu Lys Leu Tyr Asp Asp Lys Asn Ala Ser Leu
        595                 600                 605

Gly Leu Val Gly Thr His Asn Gly Gln Ile Gly Asn Asp Pro Asn Arg
    610                 615                 620

Asp Ile Leu Ile Ala Ser Asn Trp Tyr Phe Asn His Leu Lys Asp Lys
625                 630                 635                 640
Ile Leu Gly Cys Asp Trp Tyr Phe Val Pro Thr Asp Glu Gly Trp Thr
                645                 650                 655
Asn Asp Leu Gln
            660

<210> SEQ ID NO 13
<211> LENGTH: 210
<212> TYPE: PRT
<213> ORGANISM: Corynebacterium diphtheriae

<400> SEQUENCE: 13

Ser Val Gly Ser Ser Leu Ser Cys Ile Asn Leu Asp Trp Asp Val Ile
1               5                   10                  15

Arg Asp Lys Thr Lys Thr Lys Ile Glu Ser Leu Lys Glu His Gly Pro
            20                  25                  30
```

-continued

```
Ile Lys Asn Lys Met Ser Glu Ser Pro Asn Lys Thr Val Ser Glu Glu
            35                  40                  45

Lys Ala Lys Gln Tyr Leu Glu Glu Phe His Gln Thr Ala Leu Glu His
 50                  55                  60

Pro Glu Leu Ser Glu Leu Lys Thr Val Thr Gly Thr Asn Pro Val Phe
 65                  70                  75                  80

Ala Gly Ala Asn Tyr Ala Ala Trp Ala Val Asn Val Ala Gln Val Ile
                85                  90                  95

Asp Ser Glu Thr Ala Asp Asn Leu Glu Lys Thr Thr Ala Ala Leu Ser
            100                 105                 110

Ile Leu Pro Gly Ile Gly Ser Val Met Gly Ile Ala Asp Gly Ala Val
            115                 120                 125

His His Asn Thr Glu Glu Ile Val Ala Gln Ser Ile Ala Leu Ser Ser
        130                 135                 140

Leu Met Val Ala Gln Ala Ile Pro Leu Val Gly Glu Leu Val Asp Ile
145                 150                 155                 160

Gly Phe Ala Ala Tyr Asn Phe Val Glu Ser Ile Ile Asn Leu Phe Gln
                165                 170                 175

Val Val His Asn Ser Tyr Asn Arg Pro Ala Tyr Ser Pro Gly His Lys
            180                 185                 190

Thr Gln Pro Phe Leu His Asp Gly Tyr Ala Val Ser Trp Asn Thr Val
        195                 200                 205

Arg Ser
    210

<210> SEQ ID NO 14
<211> LENGTH: 1092
<212> TYPE: PRT
<213> ORGANISM: Clostridium botulinum

<400> SEQUENCE: 14

Leu Val Ser Lys Phe Glu Asn Ser Val Lys Asn Ser Asn Lys Asn Tyr
 1               5                  10                  15

Phe Thr Ile Asn Gly Leu Met Gly Tyr Tyr Phe Glu Asn Asp Phe Phe
                20                  25                  30

Asn Leu Asn Ile Ile Ser Pro Thr Leu Asp Gly Asn Leu Thr Phe Ser
            35                  40                  45

Lys Glu Asp Ile Asn Ser Ile Leu Gly Asn Lys Ile Ile Lys Ser Ala
 50                  55                  60

Arg Trp Ile Gly Leu Ile Lys Pro Ser Ile Thr Gly Glu Tyr Ile Leu
 65                  70                  75                  80

Ser Thr Asn Ser Pro Asn Cys Arg Val Glu Leu Asn Gly Glu Ile Phe
                85                  90                  95

Asn Leu Ser Leu Asn Thr Ser Asn Thr Val Asn Leu Ile Gln Gly Asn
            100                 105                 110

Val Tyr Asp Ile Arg Ile Glu Gln Leu Met Ser Glu Asn Gln Leu Leu
        115                 120                 125

Lys Asn Tyr Glu Gly Ile Lys Leu Tyr Trp Glu Thr Ser Asp Ile Ile
        130                 135                 140

Lys Glu Ile Ile Pro Ser Glu Val Leu Leu Pro Asn Tyr Ser Asn
145                 150                 155                 160

Thr Asn Glu Lys Ser Lys Phe Ile Pro Asn Asn Thr Leu Phe Ser Asn
                165                 170                 175

Ala Lys Leu Lys Ala Asn Ala Asn Arg Asp Thr Asp Arg Asp Gly Ile
            180                 185                 190
```

```
Pro Asp Glu Trp Glu Ile Asn Gly Tyr Thr Val Met Asn Gln Lys Ala
        195                 200                 205
Val Ala Trp Asp Asp Lys Phe Ala Ala Asn Gly Tyr Lys Lys Tyr Val
    210                 215                 220
Ser Asn Pro Phe Lys Pro Cys Thr Ala Asn Asp Pro Tyr Thr Asp Phe
225                 230                 235                 240
Glu Lys Val Ser Gly Gln Ile Asp Pro Ser Val Ser Met Val Ala Arg
                245                 250                 255
Asp Pro Met Ile Ser Ala Tyr Pro Ile Val Gly Val Gln Met Glu Arg
            260                 265                 270
Leu Val Val Ser Lys Ser Glu Thr Ile Thr Gly Asp Ser Thr Lys Ser
        275                 280                 285
Met Ser Lys Ser Thr Ser His Ser Ser Thr Asn Ile Asn Thr Val Gly
    290                 295                 300
Ala Glu Val Ser Gly Ser Leu Gln Leu Ala Gly Gly Ile Phe Pro Val
305                 310                 315                 320
Phe Ser Met Ser Ala Ser Ala Asn Tyr Ser His Thr Trp Gln Asn Thr
                325                 330                 335
Ser Thr Val Asp Asp Thr Thr Gly Glu Ser Phe Ser Gln Gly Leu Ser
            340                 345                 350
Ile Asn Thr Gly Glu Ser Ala Tyr Ile Asn Pro Asn Ile Arg Tyr Tyr
        355                 360                 365
Asn Thr Gly Thr Ala Pro Val Tyr Asn Val Thr Pro Thr Thr Thr Ile
    370                 375                 380
Val Ile Asp Lys Gln Ser Val Ala Thr Ile Lys Gly Gln Glu Ser Leu
385                 390                 395                 400
Ile Gly Asp Tyr Leu Asn Pro Gly Gly Thr Tyr Pro Ile Ile Gly Glu
                405                 410                 415
Pro Pro Met Ala Leu Asn Thr Met Asp Gln Phe Ser Ser Arg Leu Ile
            420                 425                 430
Pro Ile Asn Tyr Asn Gln Leu Lys Ser Ile Asp Asn Gly Gly Thr Val
        435                 440                 445
Met Leu Ser Thr Ser Gln Phe Thr Gly Asn Phe Ala Lys Tyr Asn Ser
    450                 455                 460
Asn Gly Asn Leu Val Thr Asp Gly Asn Asn Trp Gly Pro Tyr Leu Gly
465                 470                 475                 480
Thr Ile Lys Ser Thr Thr Ala Ser Leu Thr Leu Ser Phe Ser Gly Gln
                485                 490                 495
Thr Thr Gln Val Ala Val Val Ala Pro Asn Phe Ser Asp Pro Glu Asp
            500                 505                 510
Lys Thr Pro Lys Leu Thr Leu Glu Gln Ala Leu Val Lys Ala Phe Ala
        515                 520                 525
Leu Glu Lys Lys Asn Gly Lys Phe Tyr Phe His Gly Leu Glu Ile Ser
    530                 535                 540
Lys Asn Glu Lys Ile Gln Val Phe Leu Asp Ser Asn Thr Asn Asn Asp
545                 550                 555                 560
Phe Glu Asn Gln Leu Lys Asn Thr Ala Asp Lys Asp Ile Met His Cys
                565                 570                 575
Ile Ile Lys Arg Asn Met Asn Ile Leu Val Lys Val Ile Thr Phe Lys
            580                 585                 590
Glu Asn Ile Ser Ser Ile Asn Ile Ile Asn Asp Thr Asn Phe Gly Val
        595                 600                 605
```

-continued

```
Gln Ser Met Thr Gly Leu Ser Asn Arg Ser Lys Gly Gln Asp Gly Ile
    610                 615                 620
Tyr Arg Ala Ala Thr Ala Phe Ser Phe Lys Ser Lys Glu Leu Lys
625                 630                 635                 640
Tyr Pro Glu Gly Arg Tyr Arg Met Arg Phe Val Ile Gln Ser Tyr Glu
                645                 650                 655
Pro Phe Thr Thr Met Ser Tyr Thr Asn Asp Lys Ile Leu Ile Leu Tyr
                660                 665                 670
Phe Asn Lys Leu Tyr Lys Ile Lys Asp Asn Ser Ile Leu Asp Met
            675                 680                 685
Arg Tyr Glu Asn Asn Lys Phe Ile Asp Ile Ser Gly Tyr Gly Ser Asn
            690                 695                 700
Ile Ser Ile Asn Gly Asp Val Tyr Ile Tyr Ser Thr Asn Arg Asn Gln
705                 710                 715                 720
Phe Gly Ile Tyr Ser Ser Lys Pro Ser Glu Val Asn Ile Ala Gln Asn
                725                 730                 735
Asn Asp Ile Ile Tyr Asn Gly Arg Tyr Gln Asn Phe Ser Ile Ser Phe
                740                 745                 750
Trp Val Arg Ile Pro Lys Tyr Phe Asn Lys Val Asn Leu Asn Asn Glu
            755                 760                 765
Tyr Thr Ile Ile Asp Cys Ile Arg Asn Asn Asn Ser Gly Trp Lys Ile
770                 775                 780
Ser Leu Asn Tyr Asn Lys Ile Ile Trp Thr Leu Gln Asp Thr Ala Gly
785                 790                 795                 800
Asn Asn Gln Lys Leu Val Phe Asn Tyr Thr Gln Met Ile Ser Ile Ser
                805                 810                 815
Asp Tyr Ile Asn Lys Trp Ile Phe Val Thr Ile Thr Asn Asn Arg Leu
            820                 825                 830
Gly Asn Ser Arg Ile Tyr Ile Asn Gly Asn Leu Ile Asp Glu Lys Ser
            835                 840                 845
Ile Ser Asn Leu Gly Asp Ile His Val Ser Asp Asn Ile Leu Phe Lys
850                 855                 860
Ile Val Gly Cys Asn Asp Thr Arg Tyr Val Gly Ile Arg Tyr Phe Lys
865                 870                 875                 880
Val Phe Asp Thr Glu Leu Gly Lys Thr Glu Ile Glu Thr Leu Tyr Ser
                885                 890                 895
Asp Glu Pro Asp Pro Ser Ile Leu Lys Asp Phe Trp Gly Asn Tyr Leu
                900                 905                 910
Leu Tyr Asn Lys Arg Tyr Tyr Leu Leu Asn Leu Leu Arg Thr Asp Lys
            915                 920                 925
Ser Ile Thr Gln Asn Ser Asn Phe Leu Asn Ile Asn Gln Gln Arg Gly
    930                 935                 940
Val Tyr Gln Lys Pro Asn Ile Phe Ser Asn Thr Arg Leu Tyr Thr Gly
945                 950                 955                 960
Val Glu Val Ile Ile Arg Lys Asn Gly Ser Thr Asp Ile Ser Asn Thr
                965                 970                 975
Asp Asn Phe Val Arg Lys Asn Asp Leu Ala Tyr Ile Asn Val Val Asp
            980                 985                 990
Arg Asp Val Glu Tyr Arg Leu Tyr Ala Asp Ile Ser Ile Ala Lys Pro
    995                 1000                1005
Glu Lys Ile Ile Lys Leu Ile Arg Thr Ser Asn Ser Asn Asn Ser
    1010                1015                1020
Leu Gly Gln Ile Ile Val Met Asp Ser Ile Gly Asn Asn Cys Thr
```

```
                       1025                1030                1035
Met Asn  Phe Gln Asn Asn  Gly Gly Asn Ile Gly  Leu Leu Gly
    1040                 1045                 1050

Phe His  Ser Asn Asn Leu  Val Ala Ser Ser Trp  Tyr Tyr Asn Asn
    1055                 1060                 1065

Ile Arg  Lys Asn Thr Ser  Ser Asn Gly Cys Phe  Trp Ser Phe Ile
    1070                 1075                 1080

Ser Lys  Glu His Gly Trp  Gln Glu Asn
    1085                 1090
```

<210> SEQ ID NO 15
<211> LENGTH: 1032
<212> TYPE: PRT
<213> ORGANISM: Clostridium botulinum

<400> SEQUENCE: 15

```
Leu Val Ser Lys Phe Glu Asn Ser Val Lys Asn Ser Asn Lys Asn Tyr
1               5                   10                  15

Phe Thr Ile Asn Gly Leu Met Gly Tyr Tyr Phe Glu Asn Asp Phe Phe
                20                  25                  30

Asn Leu Asn Ile Ile Ser Pro Thr Leu Asp Gly Asn Leu Thr Phe Ser
            35                  40                  45

Lys Glu Asp Ile Asn Ser Ile Leu Gly Asn Lys Ile Ile Lys Ser Ala
50                  55                  60

Arg Trp Ile Gly Leu Ile Lys Pro Ser Ile Thr Gly Glu Tyr Ile Leu
65                  70                  75                  80

Ser Thr Asn Ser Pro Asn Cys Arg Val Glu Leu Asn Gly Glu Ile Phe
                85                  90                  95

Asn Leu Ser Leu Asn Thr Ser Asn Thr Val Asn Leu Ile Gln Gly Asn
                100                 105                 110

Val Tyr Asp Ile Arg Ile Glu Gln Leu Met Ser Glu Asn Gln Leu Leu
            115                 120                 125

Lys Asn Tyr Glu Gly Ile Lys Leu Tyr Trp Glu Thr Ser Asp Ile Ile
        130                 135                 140

Lys Glu Ile Ile Pro Ser Glu Val Leu Leu Lys Pro Asn Tyr Ser Asn
145                 150                 155                 160

Thr Asn Glu Lys Ser Lys Phe Ile Pro Asn Asn Thr Leu Phe Ser Asn
                165                 170                 175

Ala Lys Leu Lys Ala Asn Ala Asn Arg Asp Thr Asp Arg Asp Gly Ile
            180                 185                 190

Pro Asp Glu Trp Glu Ile Asn Gly Tyr Thr Val Met Asn Gln Lys Ala
        195                 200                 205

Val Ala Trp Asp Asp Lys Phe Ala Ala Asn Gly Tyr Lys Lys Tyr Val
    210                 215                 220

Ser Asn Pro Phe Lys Pro Cys Thr Ala Asn Asp Pro Tyr Thr Asp Phe
225                 230                 235                 240

Glu Lys Val Ser Gly Gln Ile Asp Pro Ser Val Ser Met Val Ala Arg
                245                 250                 255

Asp Pro Met Ile Ser Ala Tyr Pro Ile Val Gly Val Gln Met Glu Arg
            260                 265                 270

Leu Val Val Ser Lys Ser Glu Thr Ile Thr Gly Asp Ser Thr Lys Ser
        275                 280                 285

Met Ser Lys Ser Thr Ser His Ser Ser Thr Asn Ile Asn Thr Val Gly
    290                 295                 300
```

```
Ala Glu Val Ser Gly Ser Leu Gln Leu Ala Gly Gly Ile Phe Pro Val
305                 310                 315                 320

Phe Ser Met Ser Ala Ser Ala Asn Tyr Ser His Thr Trp Gln Asn Thr
                325                 330                 335

Ser Thr Val Asp Asp Thr Thr Gly Glu Ser Phe Ser Gln Gly Leu Ser
            340                 345                 350

Ile Asn Thr Gly Glu Ser Ala Tyr Ile Asn Pro Asn Ile Arg Tyr Tyr
        355                 360                 365

Asn Thr Gly Thr Ala Pro Val Tyr Asn Val Thr Pro Thr Thr Thr Ile
    370                 375                 380

Val Ile Asp Lys Gln Ser Val Ala Thr Ile Lys Gly Gln Glu Ser Leu
385                 390                 395                 400

Ile Gly Asp Tyr Leu Asn Pro Gly Gly Thr Tyr Pro Ile Ile Gly Glu
                405                 410                 415

Pro Pro Met Ala Leu Asn Thr Met Asp Gln Phe Ser Ser Arg Leu Ile
                420                 425                 430

Pro Ile Asn Tyr Asn Gln Leu Lys Ser Ile Asp Asn Gly Gly Thr Val
            435                 440                 445

Met Leu Ser Thr Ser Gln Phe Thr Gly Asn Phe Ala Lys Tyr Asn Ser
        450                 455                 460

Asn Gly Asn Leu Val Thr Asp Gly Asn Asn Trp Gly Pro Tyr Leu Gly
465                 470                 475                 480

Thr Ile Lys Ser Thr Thr Ala Ser Leu Thr Leu Ser Phe Ser Gly Gln
                485                 490                 495

Thr Thr Gln Val Ala Val Val Ala Pro Asn Phe Ser Asp Pro Glu Asp
            500                 505                 510

Lys Thr Pro Lys Leu Thr Leu Glu Gln Ala Leu Val Lys Ala Phe Ala
        515                 520                 525

Leu Glu Lys Lys Asn Gly Lys Phe Tyr Phe His Gly Leu Glu Ile Ser
    530                 535                 540

Lys Asn Glu Lys Ile Gln Val Phe Leu Asp Ser Asn Thr Asn Asn Asp
545                 550                 555                 560

Phe Glu Asn Gln Leu Lys Asn Thr Ala Asp Lys Asp Ile Met His Cys
                565                 570                 575

Ile Ile Lys Arg Asn Met Asn Ile Leu Val Lys Val Ile Thr Phe Lys
                580                 585                 590

Glu Asn Ile Ser Ser Ile Asn Thr Met Ser Tyr Thr Asn Asp Lys Ile
            595                 600                 605

Leu Ile Leu Tyr Phe Asn Lys Leu Tyr Lys Lys Ile Lys Asp Asn Ser
        610                 615                 620

Ile Leu Asp Met Arg Tyr Glu Asn Asn Lys Phe Ile Asp Ile Ser Gly
625                 630                 635                 640

Tyr Gly Ser Asn Ile Ser Ile Asn Gly Asp Val Tyr Ile Tyr Ser Thr
                645                 650                 655

Asn Arg Asn Gln Phe Gly Ile Tyr Ser Ser Lys Pro Ser Glu Val Asn
            660                 665                 670

Ile Ala Gln Asn Asn Asp Ile Ile Tyr Asn Gly Arg Tyr Gln Asn Phe
        675                 680                 685

Ser Ile Ser Phe Trp Val Arg Ile Pro Lys Tyr Phe Asn Lys Val Asn
    690                 695                 700

Leu Asn Asn Glu Tyr Thr Ile Ile Asp Cys Ile Arg Asn Asn Asn Ser
705                 710                 715                 720

Gly Trp Lys Ile Ser Leu Asn Tyr Asn Lys Ile Ile Trp Thr Leu Gln
```

```
                725                 730                 735
Asp Thr Ala Gly Asn Asn Gln Lys Leu Val Phe Asn Tyr Thr Gln Met
            740                 745                 750

Ile Ser Ile Ser Asp Tyr Ile Asn Lys Trp Ile Phe Val Thr Ile Thr
                755                 760                 765

Asn Asn Arg Leu Gly Asn Ser Arg Ile Tyr Ile Asn Gly Asn Leu Ile
            770                 775                 780

Asp Glu Lys Ser Ile Ser Asn Leu Gly Asp Ile His Val Ser Asp Asn
785                 790                 795                 800

Ile Leu Phe Lys Ile Val Gly Cys Asn Asp Thr Arg Tyr Val Gly Ile
                805                 810                 815

Arg Tyr Phe Lys Val Phe Asp Thr Glu Leu Gly Lys Thr Glu Ile Glu
            820                 825                 830

Thr Leu Tyr Ser Asp Glu Pro Asp Pro Ser Ile Leu Lys Asp Phe Trp
            835                 840                 845

Gly Asn Tyr Leu Leu Tyr Asn Lys Arg Tyr Tyr Leu Leu Asn Leu Leu
            850                 855                 860

Arg Thr Asp Lys Ser Ile Thr Gln Asn Ser Asn Phe Leu Asn Ile Asn
865                 870                 875                 880

Gln Gln Arg Gly Val Tyr Gln Lys Pro Asn Ile Phe Ser Asn Thr Arg
                885                 890                 895

Leu Tyr Thr Gly Val Glu Val Ile Ile Arg Lys Asn Gly Ser Thr Asp
            900                 905                 910

Ile Ser Asn Thr Asp Asn Phe Val Arg Lys Asn Asp Leu Ala Tyr Ile
            915                 920                 925

Asn Val Val Asp Arg Asp Val Glu Tyr Arg Leu Tyr Ala Asp Ile Ser
            930                 935                 940

Ile Ala Lys Pro Glu Lys Ile Ile Lys Leu Ile Arg Thr Ser Asn Ser
945                 950                 955                 960

Asn Asn Ser Leu Gly Gln Ile Ile Val Met Asp Ser Ile Gly Asn Asn
                965                 970                 975

Cys Thr Met Asn Phe Gln Asn Asn Asn Gly Gly Asn Ile Gly Leu Leu
            980                 985                 990

Gly Phe His Ser Asn Asn Leu Val Ala Ser Ser Trp Tyr Tyr Asn Asn
            995                1000                1005

Ile Arg Lys Asn Thr Ser Ser Asn Gly Cys Phe Trp Ser Phe Ile
          1010                1015                1020

Ser Lys Glu His Gly Trp Gln Glu Asn
          1025                1030

<210> SEQ ID NO 16
<211> LENGTH: 1112
<212> TYPE: PRT
<213> ORGANISM: Artificial Sequence
<220> FEATURE:
<223> OTHER INFORMATION: synthetic construct

<400> SEQUENCE: 16

Leu Val Ser Lys Phe Glu Asn Ser Val Lys Asn Ser Asn Lys Asn Tyr
1               5                   10                  15

Phe Thr Ile Asn Gly Leu Met Gly Tyr Tyr Phe Glu Asn Asp Phe Phe
                20                  25                  30

Asn Leu Asn Ile Ile Ser Pro Thr Leu Asp Gly Asn Leu Thr Phe Ser
            35                  40                  45

Lys Glu Asp Ile Asn Ser Ile Leu Gly Asn Lys Ile Ile Lys Ser Ala
```

-continued

```
            50                  55                  60
Arg Trp Ile Gly Leu Ile Lys Pro Ser Ile Thr Gly Glu Tyr Ile Leu
 65                  70                  75                  80

Ser Thr Asn Ser Pro Asn Cys Arg Val Glu Leu Asn Gly Glu Ile Phe
                 85                  90                  95

Asn Leu Ser Leu Asn Thr Ser Asn Thr Val Asn Leu Ile Gln Gly Asn
                100                 105                 110

Val Tyr Asp Ile Arg Ile Glu Gln Leu Met Ser Glu Asn Gln Leu Leu
                115                 120                 125

Lys Asn Tyr Glu Gly Ile Lys Leu Tyr Trp Glu Thr Ser Asp Ile Ile
130                 135                 140

Lys Glu Ile Ile Pro Ser Glu Val Leu Leu Lys Pro Asn Tyr Ser Asn
145                 150                 155                 160

Thr Asn Glu Lys Ser Lys Phe Ile Pro Asn Asn Thr Leu Phe Ser Asn
                165                 170                 175

Ala Lys Leu Lys Ala Asn Ala Asn Arg Asp Thr Asp Arg Asp Gly Ile
                180                 185                 190

Pro Asp Glu Trp Glu Ile Asn Gly Tyr Thr Val Met Asn Gln Lys Ala
                195                 200                 205

Val Ala Trp Asp Asp Lys Phe Ala Ala Asn Gly Tyr Lys Lys Tyr Val
                210                 215                 220

Ser Asn Pro Phe Lys Pro Cys Thr Ala Asn Asp Pro Tyr Thr Asp Phe
225                 230                 235                 240

Glu Lys Val Ser Gly Gln Ile Asp Pro Ser Val Ser Met Val Ala Arg
                245                 250                 255

Asp Pro Met Ile Ser Ala Tyr Pro Ile Val Gly Val Gln Met Glu Arg
                260                 265                 270

Leu Val Val Ser Lys Ser Glu Thr Ile Thr Gly Asp Ser Thr Lys Ser
                275                 280                 285

Met Ser Lys Ser Thr Ser His Ser Ser Thr Asn Ile Asn Thr Val Gly
                290                 295                 300

Ala Glu Val Ser Gly Ser Leu Gln Leu Ala Gly Gly Ile Phe Pro Val
305                 310                 315                 320

Phe Ser Met Ser Ala Ser Ala Asn Tyr Ser His Thr Trp Gln Asn Thr
                325                 330                 335

Ser Thr Val Asp Asp Thr Thr Gly Glu Ser Phe Ser Gln Gly Leu Ser
                340                 345                 350

Ile Asn Thr Gly Glu Ser Ala Tyr Ile Asn Pro Asn Ile Arg Tyr Tyr
                355                 360                 365

Asn Thr Gly Thr Ala Pro Val Tyr Asn Val Thr Pro Thr Thr Thr Ile
                370                 375                 380

Val Ile Asp Lys Gln Ser Val Ala Thr Ile Lys Gly Gln Glu Ser Leu
385                 390                 395                 400

Ile Gly Asp Tyr Leu Asn Pro Gly Gly Thr Tyr Pro Ile Ile Gly Glu
                405                 410                 415

Pro Pro Met Ala Leu Asn Thr Met Asp Gln Phe Ser Ser Arg Leu Ile
                420                 425                 430

Pro Ile Asn Tyr Asn Gln Leu Lys Ser Ile Asp Asn Gly Gly Thr Val
                435                 440                 445

Met Leu Ser Thr Ser Gln Phe Thr Gly Asn Phe Ala Lys Tyr Asn Ser
                450                 455                 460

Asn Gly Asn Leu Val Thr Asp Gly Asn Asn Trp Gly Pro Tyr Leu Gly
465                 470                 475                 480
```

```
Thr Ile Lys Ser Thr Thr Ala Ser Leu Thr Leu Ser Phe Ser Gly Gln
                485                 490                 495
Thr Thr Gln Val Ala Val Val Ala Pro Asn Phe Ser Asp Pro Glu Asp
            500                 505                 510
Lys Thr Pro Lys Leu Thr Leu Glu Gln Ala Leu Val Lys Ala Phe Ala
            515                 520                 525
Leu Glu Lys Lys Asn Gly Lys Phe Tyr Phe His Gly Leu Glu Ile Ser
            530                 535                 540
Lys Asn Glu Lys Ile Gln Val Phe Leu Asp Ser Asn Thr Asn Asn Asp
545                 550                 555                 560
Phe Glu Asn Gln Leu Lys Asn Thr Ala Asp Lys Asp Ile Met His Cys
                565                 570                 575
Ile Ile Lys Arg Asn Met Asn Ile Leu Val Lys Val Ile Thr Phe Lys
                580                 585                 590
Glu Asn Ile Ser Ser Ile Asn Ile Ile Asn Asp Thr Asn Phe Gly Val
                595                 600                 605
Gln Ser Met Thr Gly Leu Ser Asn Arg Ser Lys Gly Gln Asp Gly Ile
                610                 615                 620
Tyr Arg Ala Ala Thr Thr Ala Phe Ser Phe Lys Ser Lys Glu Leu Lys
625                 630                 635                 640
Tyr Pro Glu Gly Arg Tyr Arg Met Arg Phe Val Ile Gln Ser Tyr Glu
                645                 650                 655
Pro Phe Thr Lys Asn Leu Asp Cys Trp Val Asp Asn Glu Glu Asp Ile
                660                 665                 670
Asp Val Ile Leu Lys Lys Ser Thr Ile Leu Asn Leu Asp Ile Asn Asn
                675                 680                 685
Asp Ile Ile Ser Asp Ile Ser Gly Phe Asn Ser Ser Val Ile Thr Tyr
                690                 695                 700
Pro Asp Ala Gln Leu Val Pro Gly Ile Asn Gly Lys Ala Ile His Leu
705                 710                 715                 720
Val Asn Asn Glu Ser Ser Glu Val Ile Val His Lys Ala Met Asp Ile
                725                 730                 735
Glu Tyr Asn Asp Met Phe Asn Asn Phe Thr Val Ser Phe Trp Leu Arg
                740                 745                 750
Val Pro Lys Val Ser Ala Ser His Leu Glu Gln Tyr Gly Thr Asn Glu
                755                 760                 765
Tyr Ser Ile Ile Ser Ser Met Lys Lys His Ser Leu Ser Ile Gly Ser
                770                 775                 780
Gly Trp Ser Val Ser Leu Lys Gly Asn Asn Leu Ile Trp Thr Leu Lys
785                 790                 795                 800
Asp Ser Ala Gly Glu Val Arg Gln Ile Thr Phe Arg Asp Leu Pro Asp
                805                 810                 815
Lys Phe Asn Ala Tyr Leu Ala Asn Lys Trp Val Phe Ile Thr Ile Thr
                820                 825                 830
Asn Asp Arg Leu Ser Ser Ala Asn Leu Tyr Ile Asn Gly Val Leu Met
                835                 840                 845
Gly Ser Ala Glu Ile Thr Gly Leu Gly Ala Ile Arg Glu Asp Asn Asn
                850                 855                 860
Ile Thr Leu Lys Leu Asp Arg Cys Asn Asn Asn Asn Gln Tyr Val Ser
865                 870                 875                 880
Ile Asp Lys Phe Arg Ile Phe Cys Lys Ala Leu Asn Pro Lys Glu Ile
                885                 890                 895
```

```
Glu Lys Leu Tyr Thr Ser Tyr Leu Ser Ile Thr Phe Leu Arg Asp Phe
            900                 905                 910

Trp Gly Asn Pro Leu Arg Tyr Asp Thr Glu Tyr Tyr Leu Ile Pro Val
            915                 920                 925

Ala Ser Ser Lys Asp Val Gln Leu Lys Asn Ile Thr Asp Tyr Met
        930                 935                 940

Tyr Leu Thr Asn Ala Pro Ser Tyr Thr Asn Gly Lys Leu Asn Ile Tyr
945                 950                 955                 960

Tyr Arg Arg Leu Tyr Asn Gly Leu Lys Phe Ile Ile Lys Arg Tyr Thr
                965                 970                 975

Pro Asn Asn Glu Ile Asp Ser Phe Val Lys Ser Gly Asp Phe Ile Lys
            980                 985                 990

Leu Tyr Val Ser Tyr Asn Asn  Glu His Ile Val Gly  Tyr Pro Lys
        995                 1000                1005

Asp Gly  Asn Ala Phe Asn Asn  Leu Asp Arg Ile Leu  Arg Val Gly
    1010                1015                1020

Tyr Asn  Ala Pro Gly Ile Pro  Leu Tyr Lys Lys Met  Glu Ala Val
    1025                1030                1035

Lys Leu  Arg Asp Leu Lys Thr  Tyr Ser Val Gln Leu  Lys Leu Tyr
    1040                1045                1050

Asp Asp  Lys Asn Ala Ser Leu  Gly Leu Val Gly Thr  His Asn Gly
    1055                1060                1065

Gln Ile  Gly Asn Asp Pro Asn  Arg Asp Ile Leu Ile  Ala Ser Asn
    1070                1075                1080

Trp Tyr  Phe Asn His Leu Lys  Asp Lys Ile Leu Gly  Cys Asp Trp
    1085                1090                1095

Tyr Phe  Val Pro Thr Asp Glu  Gly Trp Thr Asn Asp  Leu Gln
    1100                1105                1110

<210> SEQ ID NO 17
<211> LENGTH: 1052
<212> TYPE: PRT
<213> ORGANISM: Artificial Sequence
<220> FEATURE:
<223> OTHER INFORMATION: synthetic construct

<400> SEQUENCE: 17

Leu Val Ser Lys Phe Glu Asn Ser Val Lys Asn Ser Asn Lys Asn Tyr
1               5                   10                  15

Phe Thr Ile Asn Gly Leu Met Gly Tyr Tyr Phe Glu Asn Asp Phe Phe
            20                  25                  30

Asn Leu Asn Ile Ile Ser Pro Thr Leu Asp Gly Asn Leu Thr Phe Ser
        35                  40                  45

Lys Glu Asp Ile Asn Ser Ile Leu Gly Asn Lys Ile Ile Lys Ser Ala
    50                  55                  60

Arg Trp Ile Gly Leu Ile Lys Pro Ser Ile Thr Gly Glu Tyr Ile Leu
65                  70                  75                  80

Ser Thr Asn Ser Pro Asn Cys Arg Val Glu Leu Asn Gly Glu Ile Phe
                85                  90                  95

Asn Leu Ser Leu Asn Thr Ser Asn Thr Val Asn Leu Ile Gln Gly Asn
            100                 105                 110

Val Tyr Asp Ile Arg Ile Glu Gln Leu Met Ser Glu Asn Gln Leu Leu
        115                 120                 125

Lys Asn Tyr Glu Gly Ile Lys Leu Tyr Trp Glu Thr Ser Asp Ile Ile
    130                 135                 140
```

-continued

```
Lys Glu Ile Ile Pro Ser Glu Val Leu Leu Lys Pro Asn Tyr Ser Asn
145                 150                 155                 160

Thr Asn Glu Lys Ser Lys Phe Ile Pro Asn Asn Thr Leu Phe Ser Asn
                165                 170                 175

Ala Lys Leu Lys Ala Asn Ala Asn Arg Asp Thr Asp Arg Asp Gly Ile
            180                 185                 190

Pro Asp Glu Trp Glu Ile Asn Gly Tyr Thr Val Met Asn Gln Lys Ala
        195                 200                 205

Val Ala Trp Asp Asp Lys Phe Ala Ala Asn Gly Tyr Lys Lys Tyr Val
    210                 215                 220

Ser Asn Pro Phe Lys Pro Cys Thr Ala Asn Asp Pro Tyr Thr Asp Phe
225                 230                 235                 240

Glu Lys Val Ser Gly Gln Ile Asp Pro Ser Val Ser Met Val Ala Arg
                245                 250                 255

Asp Pro Met Ile Ser Ala Tyr Pro Ile Val Gly Val Gln Met Glu Arg
            260                 265                 270

Leu Val Val Ser Lys Ser Glu Thr Ile Thr Gly Asp Ser Thr Lys Ser
        275                 280                 285

Met Ser Lys Ser Thr Ser His Ser Ser Thr Asn Ile Asn Thr Val Gly
    290                 295                 300

Ala Glu Val Ser Gly Ser Leu Gln Leu Ala Gly Gly Ile Phe Pro Val
305                 310                 315                 320

Phe Ser Met Ser Ala Ser Ala Asn Tyr Ser His Thr Trp Gln Asn Thr
                325                 330                 335

Ser Thr Val Asp Asp Thr Thr Gly Glu Ser Phe Ser Gln Gly Leu Ser
            340                 345                 350

Ile Asn Thr Gly Glu Ser Ala Tyr Ile Asn Pro Asn Ile Arg Tyr Tyr
        355                 360                 365

Asn Thr Gly Thr Ala Pro Val Tyr Asn Val Thr Pro Thr Thr Thr Ile
    370                 375                 380

Val Ile Asp Lys Gln Ser Val Ala Thr Ile Lys Gly Gln Glu Ser Leu
385                 390                 395                 400

Ile Gly Asp Tyr Leu Asn Pro Gly Gly Thr Tyr Pro Ile Ile Gly Glu
                405                 410                 415

Pro Pro Met Ala Leu Asn Thr Met Asp Gln Phe Ser Ser Arg Leu Ile
            420                 425                 430

Pro Ile Asn Tyr Asn Gln Leu Lys Ser Ile Asp Asn Gly Gly Thr Val
        435                 440                 445

Met Leu Ser Thr Ser Gln Phe Thr Gly Asn Phe Ala Lys Tyr Asn Ser
    450                 455                 460

Asn Gly Asn Leu Val Thr Asp Gly Asn Asn Trp Gly Pro Tyr Leu Gly
465                 470                 475                 480

Thr Ile Lys Ser Thr Thr Ala Ser Leu Thr Leu Ser Phe Ser Gly Gln
                485                 490                 495

Thr Thr Gln Val Ala Val Val Ala Pro Asn Phe Ser Asp Pro Glu Asp
            500                 505                 510

Lys Thr Pro Lys Leu Thr Leu Glu Gln Ala Leu Val Lys Ala Phe Ala
        515                 520                 525

Leu Glu Lys Lys Asn Gly Lys Phe Tyr Phe His Gly Leu Glu Ile Ser
    530                 535                 540

Lys Asn Glu Lys Ile Gln Val Phe Leu Asp Ser Asn Thr Asn Asn Asp
545                 550                 555                 560

Phe Glu Asn Gln Leu Lys Asn Thr Ala Asp Lys Asp Ile Met His Cys
```

-continued

```
                565                 570                 575
Ile Ile Lys Arg Asn Met Asn Ile Leu Val Lys Val Ile Thr Phe Lys
            580                 585                 590

Glu Asn Ile Ser Ser Ile Asn Lys Asn Leu Asp Cys Trp Val Asp Asn
            595                 600             605

Glu Glu Asp Ile Asp Val Ile Leu Lys Lys Ser Thr Ile Leu Asn Leu
    610                 615                 620

Asp Ile Asn Asn Asp Ile Ile Ser Asp Ile Ser Gly Phe Asn Ser Ser
625                 630                 635                 640

Val Ile Thr Tyr Pro Asp Ala Gln Leu Val Pro Gly Ile Asn Gly Lys
                645                 650                 655

Ala Ile His Leu Val Asn Asn Glu Ser Ser Glu Val Ile Val His Lys
            660                 665                 670

Ala Met Asp Ile Glu Tyr Asn Asp Met Phe Asn Asn Phe Thr Val Ser
        675                 680                 685

Phe Trp Leu Arg Val Pro Lys Val Ser Ala Ser His Leu Glu Gln Tyr
    690                 695                 700

Gly Thr Asn Glu Tyr Ser Ile Ile Ser Ser Met Lys Lys His Ser Leu
705                 710                 715                 720

Ser Ile Gly Ser Gly Trp Ser Val Ser Leu Lys Gly Asn Asn Leu Ile
                725                 730                 735

Trp Thr Leu Lys Asp Ser Ala Gly Glu Val Arg Gln Ile Thr Phe Arg
            740                 745                 750

Asp Leu Pro Asp Lys Phe Asn Ala Tyr Leu Ala Asn Lys Trp Val Phe
        755                 760                 765

Ile Thr Ile Thr Asn Asp Arg Leu Ser Ser Ala Asn Leu Tyr Ile Asn
    770                 775                 780

Gly Val Leu Met Gly Ser Ala Glu Ile Thr Gly Leu Gly Ala Ile Arg
785                 790                 795                 800

Glu Asp Asn Asn Ile Thr Leu Lys Leu Asp Arg Cys Asn Asn Asn Asn
                805                 810                 815

Gln Tyr Val Ser Ile Asp Lys Phe Arg Ile Phe Cys Lys Ala Leu Asn
            820                 825                 830

Pro Lys Glu Ile Glu Lys Leu Tyr Thr Ser Tyr Leu Ser Ile Thr Phe
        835                 840                 845

Leu Arg Asp Phe Trp Gly Asn Pro Leu Arg Tyr Asp Thr Glu Tyr Tyr
    850                 855                 860

Leu Ile Pro Val Ala Ser Ser Lys Asp Val Gln Leu Lys Asn Ile
865                 870                 875                 880

Thr Asp Tyr Met Tyr Leu Thr Asn Ala Pro Ser Tyr Thr Asn Gly Lys
                885                 890                 895

Leu Asn Ile Tyr Tyr Arg Arg Leu Tyr Asn Gly Leu Lys Phe Ile Ile
            900                 905                 910

Lys Arg Tyr Thr Pro Asn Asn Glu Ile Asp Ser Phe Val Lys Ser Gly
        915                 920                 925

Asp Phe Ile Lys Leu Tyr Val Ser Tyr Asn Asn Asn Glu His Ile Val
    930                 935                 940

Gly Tyr Pro Lys Asp Gly Asn Ala Phe Asn Asn Leu Asp Arg Ile Leu
945                 950                 955                 960

Arg Val Gly Tyr Asn Ala Pro Gly Ile Pro Leu Tyr Lys Lys Met Glu
                965                 970                 975

Ala Val Lys Leu Arg Asp Leu Lys Thr Tyr Ser Val Gln Leu Lys Leu
            980                 985                 990
```

```
Tyr Asp Asp Lys Asn Ala Ser Leu  Gly Leu Val Gly Thr  His Asn Gly
        995                 1000                1005

Gln Ile  Gly Asn Asp Pro Asn  Arg Asp Ile Leu Ile  Ala Ser Asn
    1010              1015                1020

Trp Tyr  Phe Asn His Leu Lys  Asp Lys Ile Leu Gly  Cys Asp Trp
    1025              1030                1035

Tyr Phe  Val Pro Thr Asp Glu  Gly Trp Thr Asn Asp  Leu Gln
    1040              1045                1050

<210> SEQ ID NO 18
<211> LENGTH: 10
<212> TYPE: PRT
<213> ORGANISM: Artificial Sequence
<220> FEATURE:
<223> OTHER INFORMATION: synthetic construct

<400> SEQUENCE: 18

Cys Gly Ile Glu Gly Arg Ala Pro Gly Pro
1               5                   10
```

CONSTRUCTS FOR DELIVERY OF THERAPEUTIC AGENTS TO NEURONAL CELLS

This application is a 371 of PCT/GB00/04644, filed on Dec. 4, 2000, and published in English on Aug. 16, 2001.

The present invention relates to constructs for delivering therapeutic substances to neuronal cells, to manufacture and use thereof, and in particular to constructs based on clostridial neurotoxins.

There are presently few effective treatments for major disorders of the central nervous system. Such disorders include neurodegenerative diseases, stroke, epilepsy, brain tumours, infections and HIV encephalopathy, and sufferers of these diseases far outnumber the morbidity of cancer and heart disease. The number of sufferers for CNS disorders such as stroke and the neurodegenerative diseases is set to grow, particularly in developed countries where the average age of the population is increasing. As our understanding of brain pharmacology increases and the underlying pathologies of diseases are elucidated, potential therapeutic strategies become apparent. All these treatments, however, face the formidable problem of efficient delivery of therapeutics to the various neuronal cell populations involved. Vectors which can effect efficient delivery to neuronal cells are thus required for a broad range of therapeutic substances, including drugs, enzymes, growth factors, therapeutic peptides and genes.

Ischemia/reperfusion injury induced by stroke or injury is one notable example in which rapid and efficient delivery of therapeutic agents would afford considerable benefit. Neurons injured by trauma or ischemia produce elevated levels of free oxygen radicals and release large amount of glutamate. These substances in high concentration are toxic to both neurons and surrounding cells which potentiate and amplify the damage process. Agents such as superoxide dismutase or glutamine synthetase which reduce the levels of these toxic substances have been shown to reduce neuronal cell death in a variety of in vitro and in vivo ischemia models (Gorovits et al. PNAS (1997) 94, 7024-7029; Francis et al. Experimental Neurology (1997) 146, 435-443; Lim et al. Ann. Thorac. Surg. (1986) 42, 282-286; Cuevas et al. Acta Anat. (1990) 137, 303-310). A major problem in the use of such therapies is the delivery of useful concentrations of the active agent to the site of trauma. Specific neuronal vectors could therefore play an important role in targeting such compounds to neuronal cells.

Peripheral nervous system disorders, such as motor neuron disease, are further examples of diseases which would benefit from the targeted delivery of therapeutic agents. Such therapies could take the form of drug delivery or DNA delivery via gene therapy strategies.

Gene therapy holds considerable promise for the treatment of neurodegenerative diseases such as Parkinson's and Alzheimer's diseases. Most of the currently available viral and non-viral gene delivery vectors lack tissue specificity which reduces both their efficiency and safety of use. Suitable neuronal cell-specific targeting ligands are therefore required for a broad range of gene vectors to enable effective treatments for neuronal diseases to be developed.

The *botulinum* neurotoxins are a family of protein toxins whose primary site of action is the neuromuscular junction where they block the release of the transmitter acetylcholine. The action of these toxins on the peripheral nervous system of man and animals results in the syndrome botulism, which is characterised by widespread flaccid muscular paralysis (Shone (1986) in 'Natural Toxicants in Foods', Editor D. Watson, Ellis Harwood, UK). Each of the *botulinum* neurotoxins consists of two disulphide-linked subunits; a 100 kDa heavy subunit which plays a role in the initial binding and internalisation of the neurotoxin into the nerve ending (Dolly et. al. (1984) Nature, 307, 457-460) and a 50 kDa light subunit which acts intracellularly to block the exocytosis process (McInnes and Dolly (1990) Febs Lett., 261, 323-326; de Paiva and Dolly (1990) Febs Lett., 277, 171-174).

The clostridial neurotoxins are potent inhibitors of calcium-dependent neurotransmitter secretion in neuronal cells. They are currently considered to mediate this activity through a specific endoproteolytic cleavage of at least one of three vesicle or pre-synaptic membrane associated proteins VAMP, syntaxin or SNAP-25 which are central to the vesicle docking and membrane fusion events of neurotransmitter secretion. The neuronal cell targeting of tetanus and *botulinum* neurotoxins is considered to be a receptor mediated event following which the toxins become internalised and subsequently traffic to the appropriate intracellular compartment where they effect their endopeptidase activity.

Clostridial neurotoxins share a common architecture of a catalytic L-chain (LC, ca 50 kDa) disulphide linked to a receptor binding and translocating H-chain (HC, ca 100 kDa). The HC polypeptide is considered to comprise all or part of two distinct functional domains. The carboxy-terminal half of the HC, termed the $H_C$ domain (ca 50 kDa), is involved in the high affinity, neurospecific binding of the neurotoxin to cell surface receptors on the target neuron, whilst the amino-terminal half, termed the $H_N$ domain (ca 50 kDa), is considered to mediate the translocation of at least some portion of the neurotoxin across cellular membranes such that the functional activity of the LC is expressed within the target cell. The $H_N$ domain also has the property, under conditions of low pH, of forming ion-permeable channels in lipid membranes, and this may in some manner relate to its translocation function. For *botulinum* neurotoxin type A (BoNT/A) these domains are considered to reside within amino acid residues 872-1296 for the $H_C$, amino acid residues 449-871 for the $H_N$ and residues 1-448 for the LC.

It is therefore possible to provide functional definitions of the domains within the neurotoxin molecule, as follows:—

(A) clostridial neurotoxin light chain:—
   a metalloprotease exhibiting high substrate specificity for vesicle and/or plasma membrane associated proteins involved in the exocytotic process. In particular, it cleaves one or more of SNAP-25, VAMP (synaptobrevin/cellubrevin) and syntaxin.

(B) clostridial neurotoxin heavy chain $H_N$ domain:—
   a portion of the heavy chain which enables translocation of that portion of the neurotoxin molecule such that a functional expression of light chain activity occurs within a target cell.
   the domain responsible for translocation of the endopeptidase activity, following binding of neurotoxin to its specific cell surface receptor via the binding domain, into the target cell.
   the domain responsible for formation of ion-permeable pores in lipid membranes under conditions of low pH.

(c) clostridial neurotoxin heavy chain $H_C$ domain:
   a portion of the heavy chain which is responsible for binding of the native holotoxin to cell surface receptor(s) involved in the intoxicating action of clostridial toxin prior to internalisation of the toxin into the cell.

The identity of the cellular recognition markers for these toxins is currently not understood and no specific receptor species have yet been identified although Kozaki et al. have reported that synaptotagmin may be the receptor for *botulinum* neurotoxin type B. It is probable that each of the neurotoxins has a different receptor.

Tetanus toxin is structurally very similar to *botulinum* neurotoxins but its primary site of action is the central nervous system where it blocks the release of inhibitory neurotransmitters from central synapses (Renshaw cells).

Tetanus and the *botulinum* neurotoxins from most of the seven serotypes, together with their derived heavy chains, have been shown to bind a wide variety of neuronal cell types with high affinities in the nM range, e.g. *botulinum* type B neurotoxin (Evans et al. (1986) Eur. J. Biochem. 154, 409-416).

However, a major obstacle to the use of the native clostridial heavy chain fragments as delivery vectors is that their highly aggregated state in solution prevent their adequate diffusion into body tissue and hence reduces their efficiency as targeting vectors. A further significant problem with any proposed clinical use of native tetanus toxin fragments as neuronal targeting ligands for therapeutics is the existence of circulating antibodies to the toxin in the majority of the population who have been immunized against tetanus. The presence of these antibodies is likely to reduce the efficacy of constructs based on tetanus toxin fragments. Thus, clostridial neurotoxin fragments do not offer solutions to the problems identified.

The present invention is based upon the discovery of the practical difficulties in using clostridial neurotoxin-based therapeutic compositions, and the devising of modified polypeptides and hybrid polypeptides based on clostridial neurotoxin fragments that avoid the aforementioned drawbacks.

Accordingly, a first aspect of the invention provides a non-toxic polypeptide, for delivery of a therapeutic agent to a neuronal cell, comprising:—
a binding domain that binds to the neuronal cell, and
a translocation domain that translocates the therapeutic agent into the neuronal cell, wherein the translocation domain is not a $H_N$ domain of a clostridial neurotoxin and is not a fragment or derivative of a $H_N$ domain of a clostridial toxin.

The binding domain is suitably comprised of or derived from clostridial heavy chain fragments or modified clostridial heavy chain fragments. As used herein, the term "modified clostridial heavy chain fragment" means a polypeptide fragment which retains similar biological functions to the corresponding heavy chain of a *botulinum* or tetanus neurotoxin but differs in its amino acid sequence and other properties compared to the corresponding heavy chain. The invention more specifically provides such constructs which are based on fragments derived from *botulinum* and tetanus neurotoxins.

In a further aspect, the invention also provides a polypeptide, for delivery of a therapeutic agent to a neuronal cell, comprising:—
a binding domain that binds to the neuronal cell, and
a translocation domain that translocates the therapeutic agent into the neuronal cell, wherein the resulting polypeptide construct is non-aggregating.

Whether the construct is an aggregating one is usually apparent from a lack of solubility of the construct, and this may be seen upon simple visual inspection of the construct in aqueous media: non-aggregating domains result in constructs of the invention that are partially or preferably totally soluble whereas aggregating domains result in non-soluble aggregates of polypeptides having apparent sizes of many tens or even hundreds the size of a single polypeptide. Generally, the construct should be non-aggregating as measured by size on gel electrophoresis, and the size or apparent size of the construct measured should preferably be less than $5.0 \times 10^5$ daltons, more preferably less than $1.5 \times 10^5$ daltons, with the measuring being suitably carried out on native PAGE using physiological conditions.

A still further aspect of the invention provides a polypeptide, for delivery of a therapeutic agent to a neuronal cell, comprising:—
a binding domain that binds to the neuronal cell, and
a translocation domain that translocates the therapeutic agent into the neuronal cell, wherein the translocation domain is selected from (1) a $H_N$ domain of a diphtheria toxin, (2) a fragment or derivative of (1) that substantially retains the translocating activity of the $H_N$ domain of a diphtheria toxin, (3) a fusogenic peptide, (4) a membrane disrupting peptide, (5) a $H_N$ from *botulinum* toxin $C_2$ and (6) translocating fragments and derivatives of (3), (4) and (5).

It is to be noted that *botulinum* toxin $C_2$ is not a neurotoxin as it has no neuronal specificity, instead it is an enterotoxin and suitable for use in the invention to provide a non-aggregating translocation domain.

A yet further aspect of the invention provides a polypeptide, for delivery of a therapeutic agent to a neuronal cell, comprising:—
a binding domain that binds to the neuronal cell, and
a translocation domain that translocates the therapeutic agent into the neuronal cell, wherein the polypeptide has reduced affinity to neutralising antibodies to tetanus toxin compared with the affinity to such antibodies of native tetanus toxin heavy chain.

The above aspects may singly or in any combination be exhibited by polypeptides of the invention and thus a typical preferred polypeptide of the invention (i) lacks the neurotoxic activities of *botulinum* and tetanus toxins, (ii) displays high affinity to neuronal cells corresponding to the affinity of a clostridial neurotoxin for those cells, (iii) contains a domain which can effect translocation across cell membranes, and (iv) occurs in a less aggregated state than the corresponding heavy chain from *botulinum* or tetanus toxin in physiological buffers.

A significant advantage of the polypeptides of the invention is their non-aggregated state, thus rendering them usable as soluble polypeptides where the prior art constructs were not and overcoming most if not all of the drawbacks of previous constructs based upon clostridial neurotoxins.

The polypeptides according to the invention generally include sequences from the $H_C$ domains of the *botulinum* and tetanus neurotoxins and these are combined with functional domains from other proteins, such that the essential functions of the native heavy chain, binding to neuronal cells, is retained. Thus, for example, the $H_C$ domain of *botulinum* type F neurotoxin is fused to the translocation domain derived from diphtheria toxin to give a modified clostridial heavy chain fragment. Surprisingly, such polypeptides are more useful as constructs for delivering substances to neuronal cells than are the native clostridial heavy chains.

Thus, according to a preferred aspect of the invention there is provided a polypeptide having an amino acid sequence comprising (a) a sub-sequence based on the $H_C$ fragment of *botulinum* or tetanus neurotoxin, and (b) a sub-sequence based on a translocation domain, e.g. from diphtheria toxin, that is not derived from a clostridial neurotoxin, and wherein the said polypeptide (i) lacks the neurotoxin activities of *botulinum* and tetanus toxins, (ii) displays high affinity to neuronal cells, (iii) contains a domain which can effect translocation across cell membranes and (iv) occurs in a less aggregated state than the corresponding heavy chain of *botulinum* or tetanus toxin in physiological buffers.

The modified clostridial heavy chain is suitably produced by combining the binding domain ($H_C$ domain) of a clostridial neurotoxin with a non-clostridial translocation domain. Thus, for example, a modified clostridial heavy chain fragment may be constructed from the translocation domain of diphtheria toxin (residues 194-386) fused to the $H_C$ domain of a *botulinum* toxin (e.g. type F $H_C$ fragment, residues 865-1278; type A $H_C$ fragment, residues 872-1296).

In another embodiment of the invention, the modified clostridial heavy chain is produced by combining the $H_C$ domain of a clostridial neurotoxin with a membrane disrupting peptide which functions as a translocation domain, suitably a viral peptide. Thus, for example, a modified clostridial heavy chain fragment may be constructed by combining the $H_C$ domain of a *botulinum* toxin with a peptide based on influenza virus haemagglutinin HA2 (residues 1-23).

The polypeptides of the invention have properties which make them useful as neuronal targeting ligands; they are non-toxic and yet retain the specific, high affinity binding to neuronal cells displayed by the *botulinum* or tetanus toxins. Unlike the native clostridial heavy chains, however, the modified clostridial heavy chains occur in a less aggregated state in solution which improves their access to neuronal cells. The preferred constructs are soluble in aqueous solution, in contrast to the highly aggregated state of the prior art constructs.

In another aspect of the invention, there is provided a modified tetanus heavy chain fragment which, in addition to the properties of modified heavy chains defined above, has the added advantage in that it has reduced affinity to neutralizing antibodies, present as a result of anti-tetanus inoculation, compared to the native tetanus toxin heavy chain. The polypeptides according to this aspect of the invention generally include subsequences derived from the heavy chain of tetanus toxin (residues 458-1315) and from which epitopes responsible for the immunogenicity of tetanus toxin have optionally been reduced or removed. Thus, for example, it is desirable to eliminate immunogenic epitopes associated with $H_C$ domain as well as that of the $H_N$ domain. Although it is possible to eliminate epitopes by deleting small numbers of amino acids (e.g. less than 20 or preferably less than 10 amino acids), it has been found that epitopes associated with immunogenicity of tetanus toxin heavy chain can be reduced more rigorously by replacing a large number of amino acid residues (e.g. at least 100, at least 200 and preferably 400 or more residues) with amino acid sequences from other toxins.

Thus according to a preferred aspect of the invention related to modified tetanus heavy chains, there is provided a polypeptide having an amino sequence comprising (a) an $H_N$ domain derived from a non-clostridial source (e.g. diphtheria toxin), (b) one or more subsequences derived from the sequence of a *botulinum* $H_C$, and (c) one or more subsequences derived from the sequence of tetanus toxin $H_C$, and wherein said polypeptide (i) lacks the neurotoxin activities of *botulinum* and tetanus toxins, (ii) displays high affinity to neuronal cells corresponding to the neuronal binding of tetanus neurotoxin, (iii) contains a domain which can effect translocation across cell membranes and (iv) has low affinity to neutralizing antibodies to tetanus toxin which are present as result of anti-tetanus inoculation.

This latter modified tetanus heavy chain fragment can be produced by combining the binding domain ($H_C$ domain) of tetanus neurotoxin with a non-clostridial translocation domain. Thus, for example, a modified tetanus heavy chain fragment may be constructed from the translocation domain of diphtheria toxin (residues 194-386) fused to the $H_C$ domain of a tetanus toxin (residues 865-1315).

In another embodiment of the invention the modified tetanus heavy chain is derived a non-clostridial translocation domain fused to the $H_C$ domain of a *botulinum* toxin into which the minimal domains of tetanus toxin are inserted to confer tetanus toxin-like binding activity onto the resulting hybrid. Thus, for example a modified tetanus heavy chain may be constructed from the translocation domain of diphtheria toxin (residues 194-386) fused to the $H_C$ domain of a *botulinum* type F fragment (residues 865-1278) in which residues 1097-1273 of the latter have been replaced by homologous sequences from tetanus toxin.

The modified tetanus heavy chains have properties which make them useful as neuronal targeting ligands; they are non-toxic and yet retain the specific, high affinity binding to neuronal cells displayed by tetanus toxin. Unlike native tetanus toxin binding fragments, however, the modified clostridial binding fragments have different immunogenic properties which makes them more useful clinically. Specifically, the different immunogenic properties of the modified clostridial binding fragments of the invention significantly reduce the problems caused by existing antibodies to native tetanus toxin sequences.

While the use of modified heavy chains based on *botulinum* neurotoxins as neuronal targeting ligands does not suffer from the problem of pre-existing circulating antibodies, tetanus toxin is unique amongst the clostridial toxins in that it has selectivity to inhibitory neurons (e.g. Renshaw cells) and as such the modified tetanus toxin heavy chains are valuable targeting ligands for this class of neuron. Tetanus toxin also has the property that it can retrograde transport from the peripheral to the central nervous system.

In another embodiment of the invention, the modified clostridial heavy chain fragment is fused to a linker peptide via the N-terminus of the translocation domain to which a polypeptide payload may be attached. An examples of such a linker peptide is the sequence CGLVPAGSGP (SEQ ID NO:1) which contains the thrombin protease cleavage site and a cysteine residue for disulphide bridge formation. Such a peptide linker allows production of a recombinant fusion protein comprising a polypeptide therapeutic molecule fused by the linker peptide to the N-terminus of the modified clostridial heavy chain fragment. The latter single chain fusion protein may then be treated with thrombin to give a dichain protein in which the polypeptide therapeutic is linked to the translocation domain of the modified clostridial heavy chain fragment by a disulphide link. In another example of a linker peptide in which the translocation domain does not contain a free cysteine residue near its C-terminus, such as is the case when the translocation domain is a fusogenic peptide, the linker peptide contains both cysteine residues required for the disulphide bridge. An example of the latter linker peptide is the amino acid sequence: CGLVPAGSGPSAGSSAC (SEQ ID NO:2).

In another embodiment of the invention, the modified clostridial heavy chain is linked to a polypeptide which may be an enzyme, growth factor, protein or peptide which has therapeutic benefits when delivered to neuronal cells. The polypeptide may be linked to the modified clostridial heavy chain by chemical means. Alternatively the polypeptide may be produced as a fusion protein linked to the modified clostridial binding fragment by recombinant technology using the linker peptides as described above. In such an example, the construct would contain the following components:— a polypeptide therapeutic substance;
a linker peptide; and
a modified clostridial heavy chain An example of a polypeptide therapeutic payload is superoxide dismutase.

In yet another embodiment of the invention, the modified clostridial heavy chain is linked directly or indirectly to DNA such that the construct is capable of delivering the DNA to neuronal cells, e.g. via the receptor for tetanus toxin. Such constructs have gene therapy applications and be used to switch on, or off, selected genes with the cell. The DNA may be contained within a liposome or be condensed via a peptide or protein. The modified clostridial heavy chain may be chemically linked to the protein that effects the DNA condensation by chemical coupling agents. Alternatively, the modified clostridial heavy chain may be produced as a fusion protein, by recombinant technology, with a peptide that can effect the condensation of DNA.

In yet another embodiment of the invention, the modified clostridial heavy chain fragment may be linked to a recombinant virus such that the modified virus has an altered tropism and is capable of transducing cells via the tetanus toxin receptor. Such a construct is of use to correct genetic defects within neuronal cells by switching on, or off, selected genes. The modified clostridial heavy chain fragment may be linked directly to the surface of the virus using chemical cross-linking agents. Alternatively the modified clostridial heavy chain fragment may be linked to the recombinant virus via an antibody which specifically bind to the virus. In this instance the modified clostridial binding fragment is chemically coupled to a polyclonal or monoclonal antibody which specifically recognizes a marker on the surface of the virus. A similar modified clostridial binding fragment-antibody fusion protein could be produced by recombinant technology in which the antibody component is a recombinant single chain antibody.

In yet another embodiment of the invention, the modified clostridial heavy chain fragment is linked to a drug release system such as a microparticle constructed from a suitable polymer, e.g. poly (lactide-co-glycolide), polyhydroxyalkonate, collagen, poly(divinyl-ether-comaleic anhydride, poly (styrene-co-maleic anhydride) or other polymer useful in such microparticles. The modified clostridial heavy chain fragment may be linked to the drug release system by covalent chemical coupling, or electrostatic or hydrophobic forces. The modified clostridial heavy chain fragment may also be encapsulated within the release vehicle together with the therapeutic payload provided that a portion of the modified clostridial binding fragment is exposed at the surface. Alternatively, the modified clostridial heavy chain fragment may be linked, at either the N- or C-terminal end, to a peptide or protein to facilitate coupling of the fragment to the drug release system.

Other strategies are known by which modified heavy chain binding fragments can be linked to range of therapeutic substances using a variety of established chemical cross-linking techniques, and a variety of fusion proteins can be produced containing a modified clostridial binding fragment and another polypeptide. Using these techniques a variety of substances can be targeted to neuronal cells using the modified clostridial binding fragments. Examples of possible uses of the modified clostridial binding fragments as neuronal delivery vectors are given in more detail below in Table 1.

Constructs of the invention may be introduced into either neuronal or non-neuronal tissue using methods known in the art. By subsequent specific binding to neuronal cell tissue, the targeted construct exerts its therapeutic effects. Ideally, the construct is injected near a site requiring therapeutic intervention.

The construct of the invention may be produced as a suspension, emulsion, solution or as a freeze dried powder depending on the application and properties of the therapeutic substance. The construct of the invention may be resuspended or diluted in a variety of pharmaceutically acceptable liquids depending on the application.

"Clostridial neurotoxin" means either tetanus neurotoxin or one of the seven *botulinum* neurotoxins, the latter being designated as serotypes A, B $C_1$, D, E, F or G.

"Modified clostridial heavy chain fragment" means a polypeptide fragment which binds to neuronal cell receptors in similar manner to a corresponding heavy chain derived from *botulinum* or tetanus toxins but differs in its amino acid sequence and properties compared to the corresponding fragment derived from tetanus toxin.

"Bind" in relation to the *botulinum* and tetanus heavy chain fragments, means the specific interaction between the clostridial fragment and one or more cell surface receptors or markers which results in localization of the binding fragment on the cell surface. In the case of the clostridial neurotoxins, the property of a fragment being able to 'bind' like a fragment of a given serotype can be demonstrated by competition between the ligand and the native toxin for its neuronal cell receptor.

"High affinity binding specific to neuronal cell corresponding to that of a clostridial neurotoxin" refers to the ability of a ligand to bind strongly to cell surface receptors of neuronal cells that are involved in specific binding of a given neurotoxin. The capacity of a given ligand to bind strongly to these cell surface receptors may be assessed using conventional competitive binding assays. In such assays radiolabelled clostridial neurotoxin is contacted with neuronal cells in the presence of various concentrations of non-radiolabelled ligands. The ligand mixture is incubated with the cells, at low temperature (0-3° C.) to prevent ligand internalization, during which competition between the radiolabelled clostridial neurotoxin and non-labelled ligand may occur. In such assays when the unlabelled ligand used is the same as that of the labelled neurotoxin, the radiolabelled clostridial neurotoxin will be displaced from the neuronal cell receptors as the concentration of non-labelled neurotoxin is increased. The competition curve obtained in this case will therefore be representative of the behaviour of a ligand which shows "high affinity binding specificity to neuronal cells corresponding to that of a clostridial neurotoxin", as used herein.

"Translocation domain" means a domain or fragment of a protein which effects transport of itself and/or other proteins and substances across a membrane or lipid bilayer. The latter membrane may be that of an endosome where translocation will occur during the process of receptor-mediated endocytosis. Translocation domains can frequently be identified by the property of being able to form measurable pores in lipid membranes at low pH (Shone et al. Eur J. Biochem. 167, 175-180). Examples of translocation domains are set out in more detail below in FIG. 1. In the application, translocation domains are frequently referred to as "$H_N$ domains".

"Translocation" in relation to translocation domain, means the internalization events which occur after binding to the cell surface. These events lead to the transport of substances into the cytosol of neuronal cells.

"Therapeutic substances" or "agents" mean any substance, agent or mixture thereof, which, if delivered by the modified clostridial binding fragment, would be beneficial to the treatment of neuronal diseases. Examples of these include drugs, growth factors, enzymes, and DNA packaged in various forms (e.g. modified viruses, cationic liposomes, and condensed DNA).

Also provided in the present invention are methods of manufacture of the polypeptides of the invention by expressing in a host cell a nucleic acid encoding the polypeptide, and the use of a polypeptide or a composition according to the invention in the treatment of a disease state associated with neuronal cells.

The invention is now illustrated in the following specific embodiments and accompanied by drawings in which:—

Figure 2:
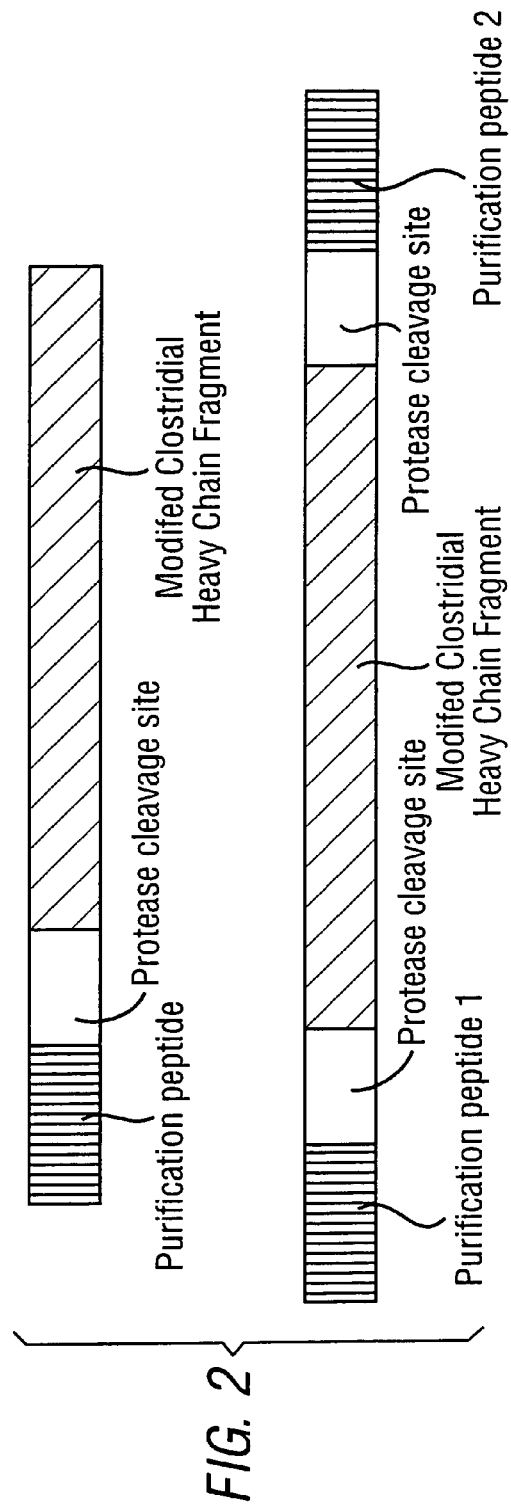
Figure 4:
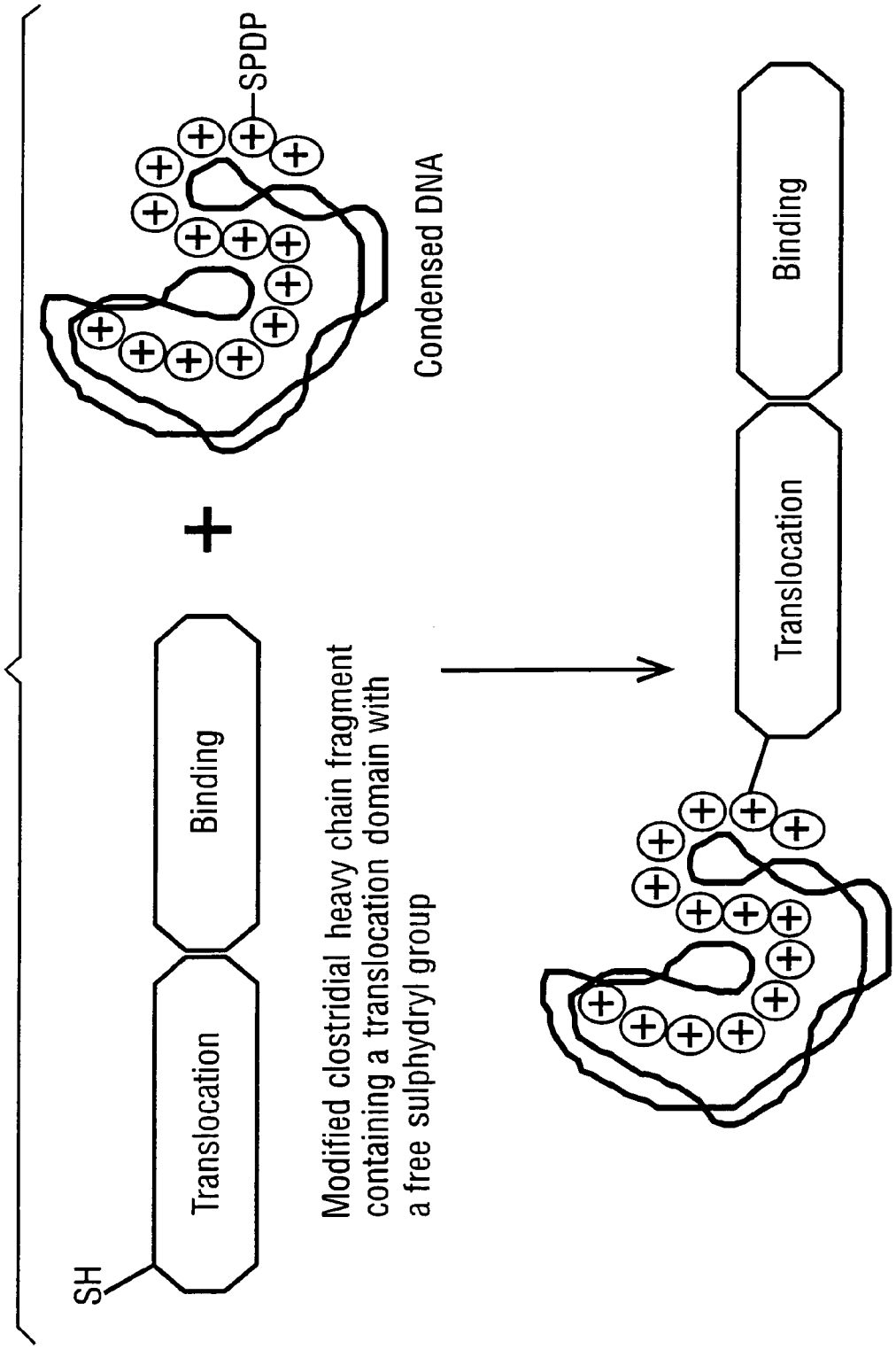
Figure 5:
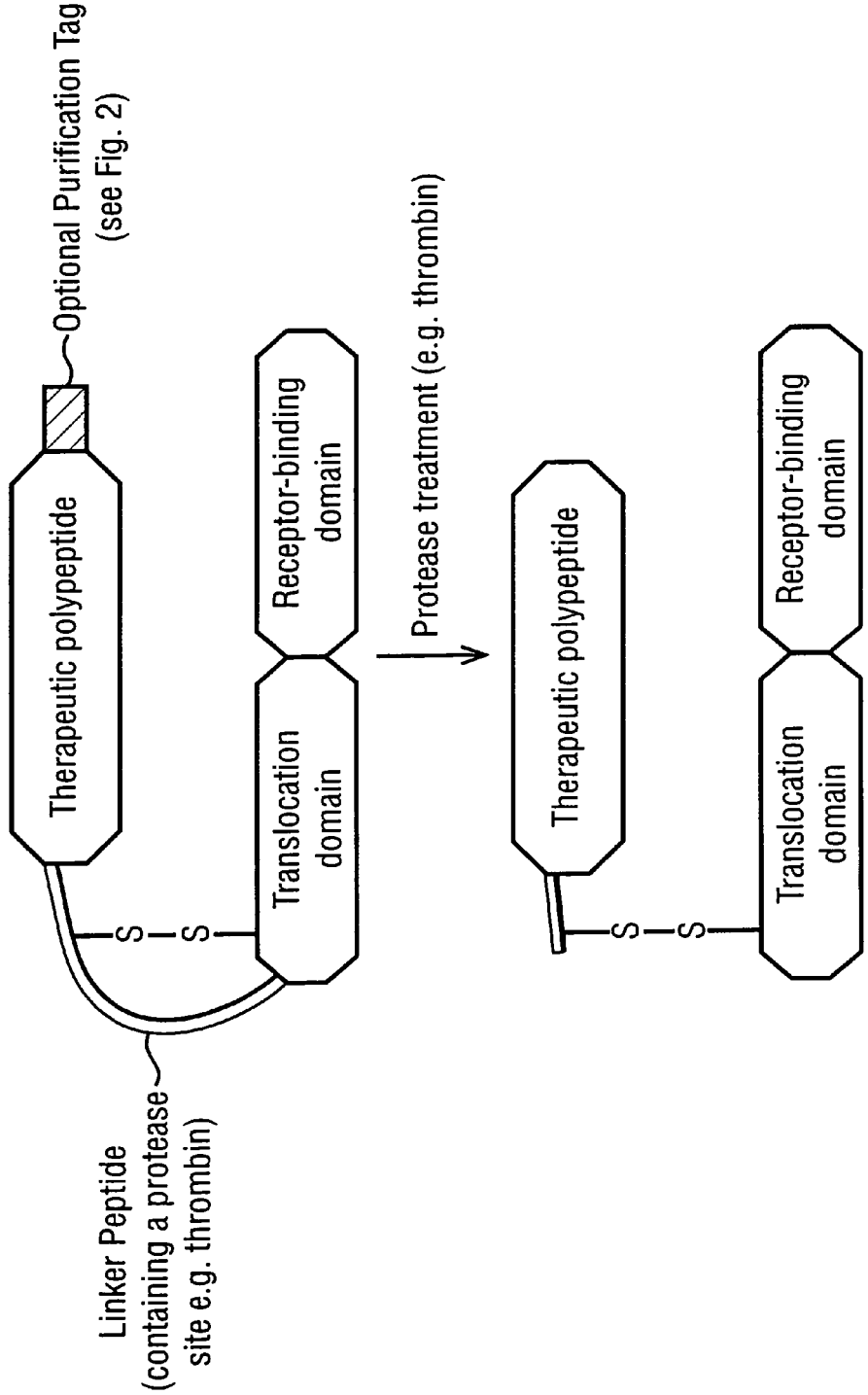

FIG. 1 shows modified clostridial heavy chain fragments produced by recombinant technology as a fusion proteins;

FIG. 2 shows modified clostridial heavy chain fragments produced by recombinant technology; fusion proteins may contain one or more purification peptide tags to assist in the purification of the protein; one or more protease cleavage sites may also be included to enable removal of the purification peptide tags; similar purification strategies may also be employed for modified clostridial binding fragments containing a translocation domain;

FIG. 3 shows linkage of a modified clostridial binding fragment to a therapeutic substance; the modified clostridial heavy chain contains a translocation domain which has a free thiol group (an example of translocation domain with this property is amino acid sequence 194-386 of diphtheria toxin), a free amino group on the therapeutic substance is modified with a cross-linking reagent (e.g. SPDP; Pierce & Warriner, UK Ltd.) which will subsequently allow conjugate formation using the free thiol present on the modified clostridial binding fragment;

FIG. 4 shows the formation of a conjugate between a modified clostridial heavy chain fragment and an oligonucleotide as described in Example 4;

FIG. 5 shows a strategy for producing a recombinant modified clostridial heavy chain as a fusion protein with a polypeptide therapeutic substance. The latter is fused to the modified clostridial heavy chain by a linker peptide. The linker peptide contains a unique protease cleavage site (e.g. that recognized by thrombin) and a cysteine residue. Examples of linker peptides are (a) CGLVPAGSGP; and (b) CGIEGRAPGP (SEQ ID NO:18). The cysteine residue forms a disulphide bridge with an another available cysteine residue on the translocation domain of the modified heavy chain fragment. If desirable, then by treatment with thrombin, a dichain product may be produced in which the polypeptide therapeutic substance is linked to the heavy chain via a disulphide bridge;

FIG. 6 shows a comparison of the binding of a modified heavy chain with that of the native neurotoxin to neuronal synaptic membranes, the modified heavy chain displaying the binding characteristics of tetanus neurotoxin as assessed by the method described in Example 7;

FIG. 7 shows the binding to neuronal membranes of a modified clostridial heavy chain based on the binding domain of botulinum type F neurotoxin; in this example, modified heavy chain contained the translocation ($H_N$) domain of diphtheria toxin and the binding ($H_C$) domain of type F neurotoxin; and FIG. 8 shows a comparison of the molecular sizes, under non-denaturing conditions, of a modified clostridial heavy chain compared to a native heavy chain; the modified clostridial heavy chain (Diphtheria $H_N$-BoNT/F $H_C$) runs as a monomer of approximately 70 kDa while a native heavy chain (from BoNT/A) runs as an aggregate of >500 kDa.

In more detail, FIG. 1 shows examples of embodiments of the invention incorporating modified clostridial heavy chain fragments.

The binding domain is derived from sequences of the clostridial neurotoxins:—
 (a) $H_C$ domains, e.g.
   BoNT/A residues 872-1296
   BoNT/B residues 859-1291
   BoNT/C residues 867-1291
   BoNT/D residues 863-1276
   BoNT/E residues 846-1252
   BoNT/F residues 865-1278
   BoNT/G residues 864-1297
   Tetanus residues 880-1315
 (b) Hybrid $H_C$ domains, e.g.
   hybrids of the $H_C$ domain of BoNT/F and tetanus
 (c) Truncated $H_C$ domains The translocation domain may be derived from a number of sources:—
 (a) Bacterial toxins, e.g. diphtheria toxin fragment B (residues 194-386)
 (b) Viral fusogenic peptides, e.g. from influenza virus haemagglutinin HA-2
 (c) Synthetic membrane disrupting peptides (e.g. Plank et al., J. Biol. Chem., 269, 12918-12924).

FIG. 2 shows examples of Recombinant Modified Clostridial Heavy Chain Fragment Fusion Proteins Showing Positions of Purification Peptide Tags and Specific Protease Cleavage Sites (by treatment with the appropriate protease, the purification peptide tags may be removed from the modified clostridial binding fragment).

Examples of purification peptides tags are:
His6
S peptide
T7 peptide
Calmodulin binding peptide
Maltose binding protein
Examples of specific protease cleavage sites are:—
Thrombin
Enterokinase
Factor X

EXAMPLE 1

Preparation and Purification of a Recombinant Modified Clostridial Heavy Chain Fragments.

Standard molecular biology protocols were used for all genetic manipulations (e.g. Sambrook et al. 1989, Molecular Cloning a Laboratory Manual, Second Edition, Cold Spring Harbor Laboratory Press, Cold Spring Harbor, N.Y.). An entirely synthetic gene encoding the $H_C$ regions of *botulinum* toxin from *C. botulinum* type F (residues 865-1278) and tetanus toxin (residues 880-1315) were generated using Recursive PCR reactions (Prodromou & Pearl 1992, *Protein Engineering,* 5: 827-829) using self-priming oligonucleotides containing the desired sequence. The codon bias and GC/AT base ratio was adjusted for ease of expression in *E.*

*coli.* Fragments were cloned sequentially into pLitmus 38 (New England Biolabs, Inc., Beverly, Mass.) to assemble the entire gene. Constructs for expression were sub-cloned into pMALc2 (NEB) replacing the BamH1-EcoR1 fragment. The ligation reactions were transformed into *E. coli* JM109 (Promega).

Plasmid DNA was amplified, purified and screened for the presence of the appropriate sequence (Ausubel et al. 1989, Current Protocols in Molecular Biology, John Wiley & Sons, New York). Gene constructions confirmed as possessing the correct sequences were then transformed into the expression host *E. coli* BL21 (DE3) (Studier & Moffatt 1986, *Journal of Molecular Biology*, 189: 113-130).

Additional sequences for adding affinity purification tags and one or more specific protease site for the subsequent removal of these affinity tags were also included in the reading frame of the gene products.

The recombinant proteins expressed in pMAL were produced with amino-terminal maltose-binding protein tags allowing proteins to be purified by affinity chromatography on amylose resin. Briefly, cultures of *E. coli* BL21 (DE3) pMALc2-$H_C$ were grown in Terrific broth-ampicillin (100 $\mu g ml^{-1}$)-kanamycin (30 $\mu g ml^{-1}$) to an $OD_{600}$ nm of 2.5-3.8, and protein expression was induced by the addition of 1 mM IPTG for approximately 2 h. Cells were lysed by freeze/thaw followed by sonication, lysates cleared by centrifugation and supernatants loaded onto an amylose resin column and eluted with maltose. All buffers used were as specified by the manufacturer. Thrombin or factor Xa protease sites were included within the protein for subsequent removal of these purification tags.

Other coding sequences which enable expression of the desired protein would also be acceptable. Other tags or linking sites may also be incorporated into the sequence. Examples of some of these options are summarized in FIG. 2.

EXAMPLE 2

Production of a Modified Clostridial Heavy Chain Fragments.

Using the techniques described in Example 1, modified clostridial heavy chain fragments was constructed by fusing domains of the $H_c$ fragments of either *botulinum* type F or tetanus neurotoxins with the translocation domain of diphtheria toxin. The amino acid sequences of examples are shown in SEQ ID NO:s 8-17, which also gives examples of modified tetanus heavy chains in which the $H_c$ fragment is a hybrid of tetanus and *botulinum* type F neurotoxin.

EXAMPLE 3

Coupling of a Modified Clostridial Heavy Chain Fragment to a Protein or an Enzyme.

The polypeptide, protein or enzyme to be linked to the modified clostridial heavy chain fragment is first derivatized with a suitable cross-linking agent. Mn-Superoxide dismutase (SOD) was modified by treatment with a 15 molar excess of SPDP (Pierce) in 0.05M Hepes buffer pH 7.0 containing 0.15M NaCl for 60 min at 25° C. The excess SPDP was removed by dialysis against the same buffer At 4° C. for 16 h. The substituted SOD was then mixed in a 1:5 molar ration with modified clostridial heavy chain fragment fused to a translocation domain derived from diphtheria toxin (see FIG. 3) and incubated at 25° C. for 16 h. After incubation the SOD-modified clostridial binding fragment conjugate was purified by gel filtration chromatography on Sephadex G200.

EXAMPLE 4

Coupling of Modified Clostridial Heavy Chain Fragment to Condensed DNA.

Poly-L-lysine ($M_r$ 1000-4000) (10 mg) to be used for the condensation of DNA was dissolved in 2 ml of 20 mM Hepes buffer pH 7.4 containing 0.15M NaCl (HBS). To this solution 0.6 mg of Sulpho-LC-SPDP (Pierce and Warriner, UK Ltd.) was added and the mixture incubated for 30 min at 25° C. The activated poly-L-lysine was then dialysed against HBS at 4° C. using a dialysis tubing of 1000 molecular weight cut-off and then diluted to 1 mg/ml using HBS.

Condensation of DNA was carried out in glass tubes. Purified plasmid DNA containing a gene encoding a therapeutic protein (or a reporter gene) under the control of a suitable promoter (e.g. CMV immediate early, or a neuronal-specific promoter e.g. neuron-specific enolase promoter) was made 1 mg/ml in HBS and added to glass tubes followed by the activated poly-L-lysine as prepared above. Activated poly-L-lysine is added in various proportions to the DNA (see Table 2) and incubated for 90 min at 25° C.

TABLE 2

Condensation of DNA with activated poly-L-lysine.

| Sample no. | DNA (µg) | Activated Poly-L-lysine | HBS |
|---|---|---|---|
| 1 | 750 | 250 | 1500 |
| 2 | 1500 | 500 | 500 |
| 3 | 500 | 250 | 1750 |
| 4 | 1000 | 500 | 1000 |

After incubation the size of the condensed DNA particles was assessed using a Brookhaven BI90 particle sizer. The incubation conditions giving the highest proportion of condensed DNA particle of less than 100 nM in diameter was used to produce DNA-modified clostridial binding fragment conjugates. Modified clostridial heavy chain was dialysed against HBS.

The dialysed fragments (100 µg) was then added to 1 ml of condensed DNA and incubated for 18 h at 25° C. to from the modified clostridial binding protein-condensed DNA construct (see FIG. 4).

EXAMPLE 5

Delivery of DNA to a Neuronal Cells via the Modified Clostridial Heavy Chain Fragment Receptor.

Modified clostridial heavy chain-condensed DNA construct described in Example 4 was diluted with 2 ml MEM serum free medium. Growth media from NG108 grown in 12 well dished was removed and 1 ml of the diluted construct added and incubated for 2 h at 37° C. in the presence of 5% $CO_2$. Growth media (1 ml) was then added to each well and the incubation continued under the same conditions for 24-48 h. After this period the cell were examined.

In experiments were the condensed DNA contained a reporter gene encoding Green Fluorescent Protein, several of the cells showed visible expression of the reporter protein illustrating successful delivery of the DNA into the neuronal cell. Various control experiments were conducted to confirm the observed transfection in NG108 cells was receptor mediated:

Transfection of NG108 cells was found to be dependent on the presence of modified clostridial heavy chain fragment within conjugates (no transfection was observed with condensed particles DNA alone)

No transfection was observed in non-neuronal cells (Vero cells) using the heavy chain-DNA conjugates.

EXAMPLE 6

Preparation of Conjugates of Modified Clostridial Heavy Chain Fragment and Microparticles Consisting of Poly (lactide-co-glycolide).

398 mg of poly (lactide co-glycolide) low internal viscosity (3000 MW)(Beohringer Mannheim,) was dissolved in 4 ml dichloromethane. This was homogenised at 2000 rpm for 150 seconds with 1 ml of buffer solution containing the therapeutic substance, such as an enzymes and/or drugs. In the case of Mn superoxide dismutase, 10 mg of the enzyme was dissolved in 10 mM Hepes buffer pH 8.0 containing 100 mM NaCl. The mixture was then added to 50 ml of 8% poly vinyl alcohol and emulsified at 2000 rpm for a further 150 seconds. The emulsion was poured into 300 ml of ultrapure distilled water at 37° C. and stirred for 30 min at 37° C. The microparticles were collected by centrifugation at 10000×g for 25 min at 20° C. and then resuspended in 300 ml water and centrifuged as above. This washing procedure was the repeated a further 4 times. After the final centrifugation the water supernatant fluid was removed and the microparticles freeze dried.

2 mg of poly (lactide-co-glycolide) microparticles were re-suspended in 1 ml of activation buffer (01 .M MES buffer, pH 6.0 containing 0.5M NaCl). Solid 1-Ethyl-3-[3-dimethylaminopropyl] carbodiimide (EDC) and N-hydroxysulphosuccinimide (sulphoNHS) were added to 2 mM and 5 mM respectively and the mixture incubated for 15 min at 25° C. The microparticles were washed by centrifugation for 1 min at 10000×g and resuspension in 1 ml of activation buffer. The wash step was repeated 4 times and then the microparticles resuspended in 1 ml of activation buffer containing 33 µM of a modified clostridial heavy chain fragment and incubated for 2 h at 25° C. The reaction was then quenched with 10 mM hydroxylamine. After 20 min at 25° C. the microparticles were washed in a suitable buffer by centrifugation as described above.

EXAMPLE 7

Demonstration of the High Affinity Binding to Neuronal Cell Tissue Displayed by Modified Heavy Chain Fragments Clostridial neurotoxins may be labelled with 125-iodine using chloramine-T and its binding to various cells assessed by standard methods such as described in Evans et al. 1986, Eur J. Biochem., 154, 409 or Wadsworth et al. 1990, Biochem. J. 268, 123). In these experiments the ability of modified clostridial heavy chain constructs to compete with native clostridial neurotoxins for receptors present on neuronal cells or brain synaptosomes was assessed. All binding experiments were carried out in binding buffers. For the *botulinum* neurotoxins this buffer consisted of: 50 mM hepes pH 7.0, 30 mM NaCl, 0.25% sucrose, 0.25% bovine serum albumin. For tetanus toxin, the binding buffer was: 0.05M MES buffer pH 6.0 containing 0.6% bovine serum albumin. In a typical binding experiment the radiolabelled clostridial neurotoxin was held at a fixed concentration of between 1-10 nM. Reaction mixtures were prepared by mixing the radiolabelled toxin with various concentrations of unlabelled neurotoxin or modified clostridial heavy chain construct. The reaction mixture were then added to neuronal cells or rat brain synaptosomes and then incubated at 0-3° C. for 2 hr. After this period the neuronal cells of synaptosomes were washed twice with binding ice-cold binding buffer and the amount of labelled clostridial neurotoxin bound to cells or synaptosomes was assessed by γ-counting.

In an experiment using a modified clostridial heavy construct which consisted of a binding domain derived from tetanus toxin and a translocation domain from diphtheria toxin, the construct was found to compete with $^{125}$I-labelled tetanus neurotoxin for neuronal cell receptors in a similar manner to unlabelled native tetanus neurotoxin (see FIG. 6). These data showed that the construct had retained binding properties of the native neurotoxin.

In a further experiment using Diphtheria $H_N$-BoNT/F $H_C$ as the modified clostridial heavy chain, the construct was found to compete with 125I-labelled BoNT/F for receptors on neuronal synaptic membranes (FIG. 7). These data indicate that the modified clostridial heavy chain retains the neuronal receptor-binding properties of BoNT/F.

EXAMPLE 8

Non-Denaturing Gel Electrophoresis to Compare the Sizes of a Native *Botulinum* Toxin Heavy Chain (Type A) with that of a Modified Clostridial Heavy Chain (Recombinant Diphtheria $H_N$-BoNT/F $H_C$)

*Botulinum* type A heavy chain was purified as described previously (Shone et al. 1985 Eur J. Biochemistry 151, 75-82) and recombinant Diphtheria $H_N$-BoNT/F $H_C$ purified as described in Examples 1 and 2. The modified clostridial heavy chain was purifies as a Maltose Binding Protein fusion with then the fusion protein removed by treatment with Factor Xa. Samples of type A heavy chain (20 µg) and Diphtheria $H_N$-BoNT/F $H_C$ (10 µg) were loaded on a 4-20% Tris-glycine polyacrylamide gel in Tris-glycine buffer. Samples were electrophoresed to equilibrium (Novex gel system; 43 volts 16 hours) and the gel stained with Coomassie blue. The results are shown in FIG. 8. The major band for Diphtheria $H_N$-BoNT/F/$H_C$ appears to migrate very close to its predicted molecular weight of approx 70 kDa. In contrast, the native type A heavy chain appears as a diffuse band at approximately 500 kDa, compared to an estimated molecular weight of 100 kDa, which suggesting the formation of large protein aggregates.

EXAMPLE 9

Recombinant Modified Heavy Chain-Superoxide Dismutase Conjugates.

Recombinant modified heavy chain-superoxide dismutase conjugates were prepared comprising a combination of the following elements:

- a bacterial superoxide dismutase, from *Bacillus stearothermophilus;*
- a linker region which allows the formation of a disulphide bond between the superoxide dismutase and the translocation domain and which also contains a unique protease cleavage site for cleavage by factor Xa or thrombin to allow the formation of a dichain molecule;
- a translocation domain from diphtheria toxin or a endosomolytic (fusogenic) peptide from influenza virus haemagglutinin); and
- a neuronal cell-specific binding domain from tetanus or *botulinum* neurotoxin type F.

The sequences of these recombinant modified heavy chain-superoxide dismutase conjugates are shown in SEQ ID NO:s 3-7.

To confirm the nature of their structure, the recombinant modified clostridial heavy chain-superoxide dismutase conjugates were converted to the dichain form by treatment with a unique protease corresponding to the cleavage site sequences within the linker region. Conjugates containing the thrombin cleavage site were treated with thrombin (20 μg per mg of conjugate) for 20 h at 37° C.; conjugates containing the factor Xa cleavage site were treated with factor Xa (20 μg per mg of conjugate) for 20 min at 22° C.

On SDS-PAGE gels, under non-reducing conditions, the conjugates appeared as a band of molecular mass approx. 120 kDa. In the presence of reducing agent (dithiothreitol) two bands were observed at approx. molecular masses 70 and 30 kDa corresponding to the modified clostridial heavy chain and superoxide dismutase respectively. These data illustrate that, after treatment with the unique protease, the conjugates consist of the latter two components which are linked by a disulphide bridge.

TABLE 1

Examples of Potential Therapeutic Uses of Modified Clostridial Binding Fragments

| Therapeutic Substance or Effector | Site and Mechanism of Action | Potential Clinical Effects |
|---|---|---|
| (a) Enzymes:- | | |
| Superoxide dismutase | Reduce oxidative stress after stroke/injury of brain or spinal cord | Reduction of neuronal damage after ischemia/reperfusion |
| Glutamine synthetase | Reduce damage by excess glutamate after stroke/injury of the brain or spinal cord | Reduction of neuronal damage after ischemia/reperfusion |
| (b) Antibodies:- | | |
| Anti-tetanus toxin | Neutralize the action of tetanus toxin at the spinal cord | Reverse the effects of intoxication by tetanus toxin |
| Anti SNARE protein (e.g. SNAP-25, VAMPs Syntaxins) | Modulate neurotransmitter release | Hyper secretory disorders |
| © Viruses/DNA | | |
| Viral gene therapy vectors (e.g. adenovirus, herpes simplex, etc.) | Replacement of defective genes within the CNS | Treatment of neurodegenerative diseases (Parkinson's' Alzheimer's ALS etc.) and other neuronal diseases |
| Non-viral vectors for gene therapy (e.g. liposomes) | Replacement of defective genes within the CNS | Treatment of neurodegenerative diseases and other neuronal diseases |
| (d) Growth factors | | |
| e.g. BDNF, CTNF, NGF | Deliver growth factors to the brain and spinal cord | Treatment of neurodegenerative diseases, promotion of neuronal growth after damage |
| (e) Anti-viral agents | Deliver anti-viral agents to the brain or spinal cord neurons | Treatment of latent viral infections within neuronal cells, e.g. HIV, herpes simplex infections |
| (f) Anti-cancer agents | Deliver cytotoxic agents to neoplastic cells of the CNS | Treatment of neuronal neoplasia |

The invention claimed is:

1. A composition comprising a therapeutic agent linked to a delivery polypeptide, SEQ ID NO. 12, wherein the delivery polypeptide is for delivery of a therapeutic agent to a neuronal cell, said delivery polypeptide comprising:
a binding domain that binds to the neuronal cell and comprises a hybrid of a *botulinum* Hc domian and a tetanus Hc domain, and
a translocation domain comprising an H$_N$ domain of a diphtheria toxin that translocates the therapeutic agent into the neuronal cell,
wherein the delivery polypeptide has the binding specificity of tetanus toxin and reduced affinity to neutralizing antibodies to tetanus toxin compared with the affinity to such antibodies of native tetanus toxin heavy chain, and wherein the therapeutic agent is for reduction of neuronal damage after ischemia/reperfusion or is for promotion of neuronal growth after damage, and wherein the therapeutic agent is a polypeptide.

2. The composition of claim 1, wherein the translocation domain is further a non-aggregating translocation domain as measured by size in physiological buffers.

3. The composition of claim 1, wherein the translocation domain is a non-aggregating translocation domain as measured by its size in physiological buffer and wherein the therapeutic agent is for reduction of neuronal damage after ischemia/reperfusion or is for promotion of neuronal growth after damage.

4. The composition of claim 1, wherein the therapeutic agent is chemically bound to said delivery polypeptide.

5. The composition of claim 1 wherein the therapeutic agent is linked to a translocation domain of said delivery polypeptide.

6. The composition of claim 1 wherein the therapeutic agent is an enzyme, growth factor, protein or peptide.

7. The composition of claim 1 wherein the therapeutic agent is produced as a fusion protein by recombinant technology methods.

8. A composition comprising a therapeutic agent linked to a delivery polypeptide, SEQ ID NO. 12, wherein the delivery polypeptide is for delivery of a therapeutic agent to a neuronal cell, said delivery polypeptide comprising:
a binding domain that binds to the neuronal cell and comprises a hybrid of a *botulinum* Hc domian and a tetanus Hc domain, and
a translocation domain comprising an H$_N$ domain of a diphtheria toxin that translocates the therapeutic agent into the neuronal cell,
wherein the delivery polypeptide has the binding specificity of tetanus toxin and reduced affinity to neutralizing antibodies to tetanus toxin compared with the affinity to such antibodies of native tetanus toxin heavy chain, and wherein the therapeutic agent is for reduction of neuronal damage after ischemia/reperfusion oris for promotion of neuronal growth after damage, and is selected from superoxide dismutase and glutamine synthetase.

* * * * *